(12) United States Patent
George et al.

(10) Patent No.: US 7,032,522 B2
(45) Date of Patent: Apr. 25, 2006

(54) OVERBED TABLE FOR USE WITH A PATIENT SUPPORT

(75) Inventors: Christopher M. George, Cincinnati, OH (US); Robert M. Zerhusen, Cincinnati, OH (US); Carl W. Riley, Milan, IN (US); Ryan A. Reeder, Brookville, IN (US); Michael E. Cerimele, Indianapolis, IN (US); David W. Hornbach, Brookville, IN (US); Michelle Larsen Walker, Lewisville, TX (US)

(73) Assignee: Hill-Rom Services, Inc., Wilmington, DE (US)

( * ) Notice: Subject to any disclaimer, the term of this patent is extended or adjusted under 35 U.S.C. 154(b) by 365 days.

(21) Appl. No.: 10/211,111

(22) Filed: Aug. 2, 2002

(65) Prior Publication Data

US 2003/0112147 A1    Jun. 19, 2003

Related U.S. Application Data

(63) Continuation-in-part of application No. 09/849,580, filed on May 4, 2001, and a continuation-in-part of application No. 09/835,002, filed on Apr. 13, 2001, now Pat. No. 6,615,744.

(60) Provisional application No. 60/310,092, filed on Aug. 3, 2001, provisional application No. 60/251,950, filed on Dec. 7, 2000, provisional application No. 60/229,136, filed on Aug. 30, 2000, provisional application No. 60/202,283, filed on May 5, 2000.

(51) Int. Cl.
*A47B 37/00* (2006.01)

(52) U.S. Cl. .................................... 108/50.01; 108/49

(58) Field of Classification Search ............. 108/50.01, 108/50.02, 3, 6, 5, 147.19, 49; 312/223.3, 312/223.6, 223.1, 223.2
See application file for complete search history.

(56) References Cited

U.S. PATENT DOCUMENTS 1,232,757 A    7/1917   Berkey (Continued)

FOREIGN PATENT DOCUMENTS

EP    0 168 158    1/1986

(Continued)

OTHER PUBLICATIONS

Hill-Rom Sales Brochure "The P633 Overbed Table", Nov. 1996.

(Continued)

*Primary Examiner*—Jose V. Chen
(74) *Attorney, Agent, or Firm*—Bose McKinney & Evans LLP

(57) ABSTRACT

An overbed table configured to support a table section above a patient support surface, such as a hospital bed. The overbed table includes a frame having a base and a substantially vertical support column for supporting the table section. In one illustrative embodiment, a display device is supported by the overbed table. In a further illustrative embodiment, a camera is supported by the overbed table.

49 Claims, 23 Drawing Sheets

U.S. PATENT DOCUMENTS

| | | |
|---|---|---|
| 1,653,657 A | 12/1927 | Pretsch |
| 1,775,877 A | 9/1930 | Wuples |
| 1,888,124 A | 11/1932 | Pulaski |
| D132,427 S | 5/1942 | Hillenbrand |
| D132,953 S | 7/1942 | Hillenbrand |
| D134,456 S | 12/1942 | Hillenbrand |
| D135,340 S | 3/1943 | Hillenbrand |
| D135,341 S | 3/1943 | Hillenbrand |
| D135,507 S | 4/1943 | Hillenbrand |
| 2,321,204 A | 6/1943 | Hillenbrand |
| 2,329,902 A | 9/1943 | Hillenbrand |
| 2,342,631 A | 2/1944 | Hillenbrand |
| 2,352,837 A | 7/1944 | Hillenbrand |
| 2,346,919 A | 8/1944 | Hillenbrand |
| 2,357,588 A | 9/1944 | Hillenbrand |
| D149,793 S | 6/1948 | Burst |
| 2,456,415 A | 12/1948 | Hillenbrand |
| 2,580,032 A | 12/1951 | Lindelof |
| 3,854,428 A | 12/1974 | Fulenkamp |
| 3,910,659 A | 10/1975 | Peterson |
| 4,401,036 A | 8/1983 | Russo et al. |
| 4,667,605 A | 5/1987 | Bastian |
| 4,715,295 A | 12/1987 | Hartman et al. |
| 4,848,710 A | 7/1989 | Newman |
| 4,852,500 A | 8/1989 | Ryburg et al. |
| 5,108,063 A | 4/1992 | Koerber, Sr. et al. |
| 5,144,898 A | 9/1992 | Posly |
| 5,287,815 A * | 2/1994 | Gross .................. 108/50.01 |
| 5,335,651 A | 8/1994 | Foster et al. |
| 5,337,682 A | 8/1994 | Wiseman |
| 5,408,940 A | 4/1995 | Winchell |
| 5,473,997 A | 12/1995 | Solomon et al. |
| 5,497,766 A | 3/1996 | Foster et al. |
| 5,544,649 A | 8/1996 | David et al. |
| 5,562,049 A | 10/1996 | Hoffman et al. |
| 5,606,917 A | 3/1997 | Cauffiel |
| D389,917 S | 1/1998 | Hornback et al. |
| 5,889,568 A | 3/1999 | Seraphim et al. |
| 6,168,250 B1 | 1/2001 | Rogov |
| 6,170,410 B1 * | 1/2001 | Gioacchini et al. ...... 108/50.01 |
| 6,237,507 B1 * | 5/2001 | Yanagisawa et al. .... 108/50.01 |
| 6,269,753 B1 * | 8/2001 | Roddan ................ 108/50.01 |
| 6,286,440 B1 * | 9/2001 | Jyringi ................. 108/50.01 |
| 6,615,744 B1 * | 9/2003 | Eckstein et al. ......... 108/147.2 |
| 6,832,560 B1 * | 12/2004 | Seiler et al. ............ 108/50.01 |

FOREIGN PATENT DOCUMENTS

| | | |
|---|---|---|
| WO | WO 94/13198 | 6/1994 |
| WO | WO 98/02107 | 1/1998 |

OTHER PUBLICATIONS

Hill-Rom Brochure "Overbed Tables", 2000.

* cited by examiner

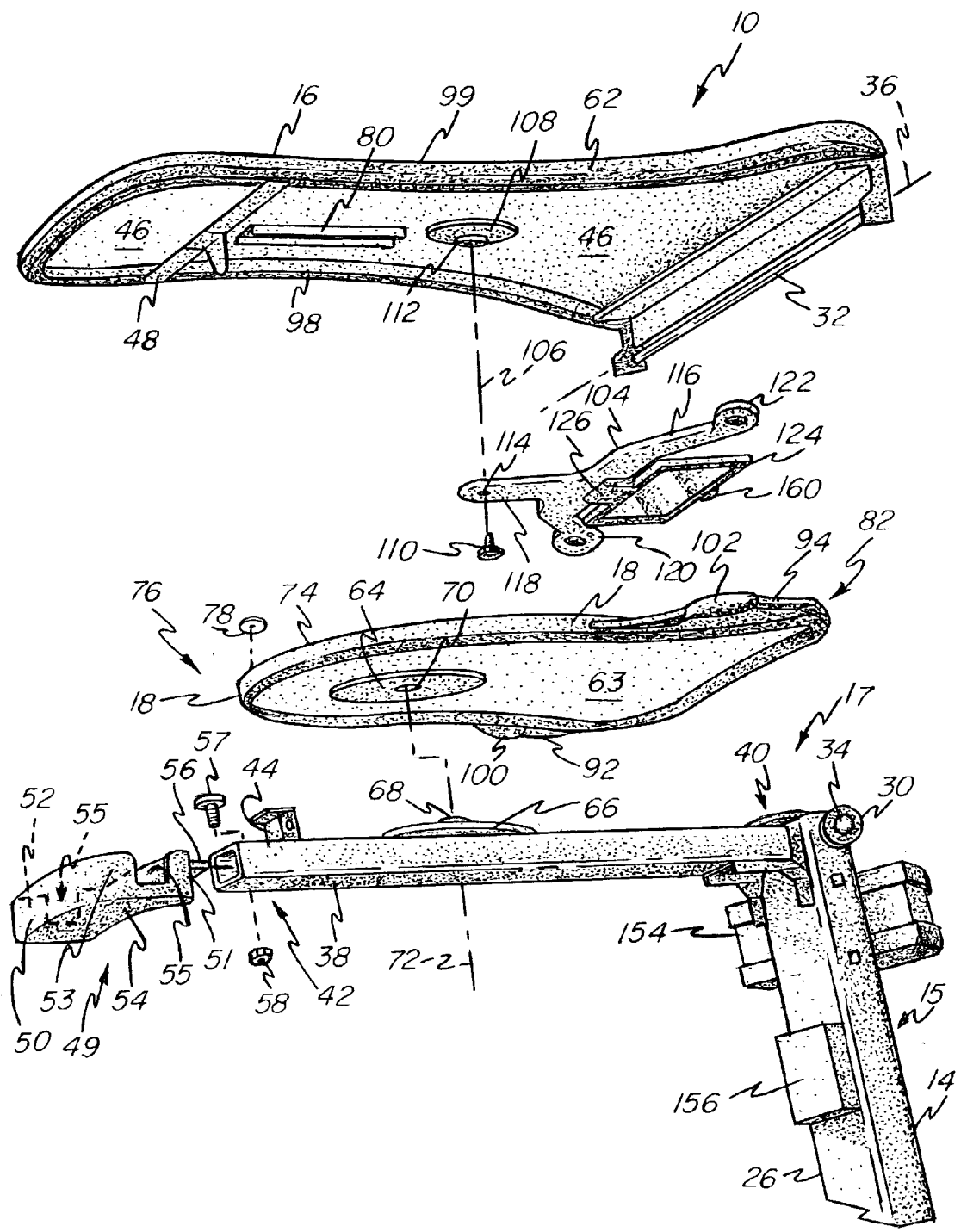

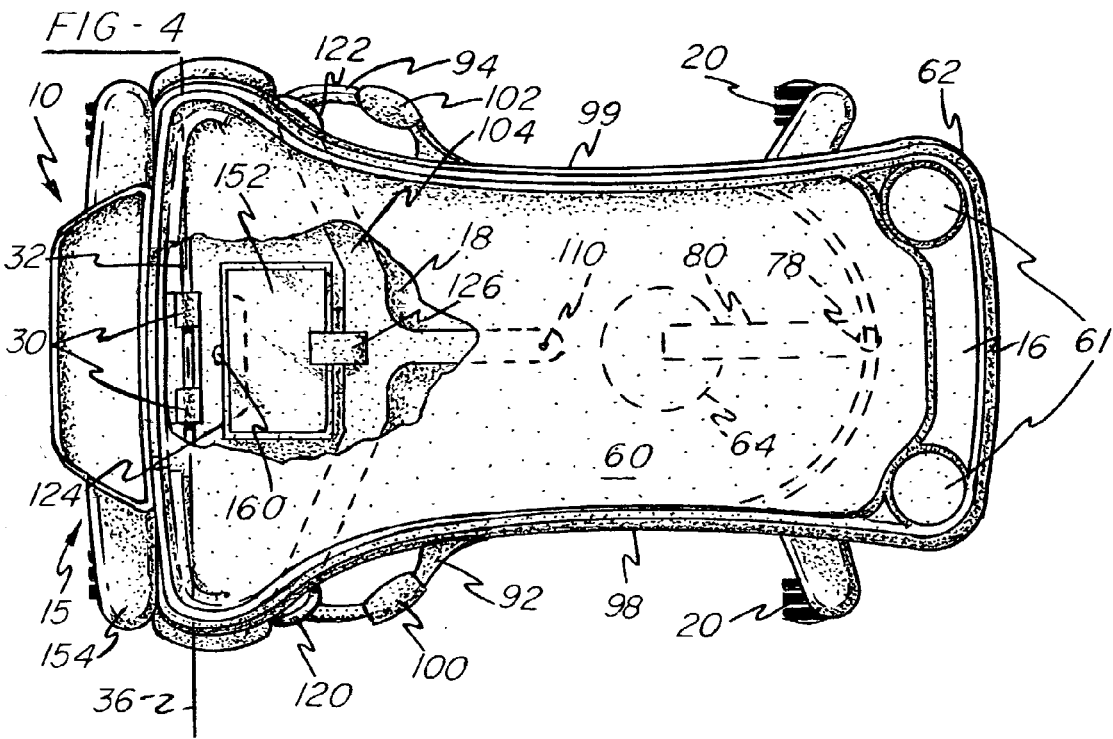
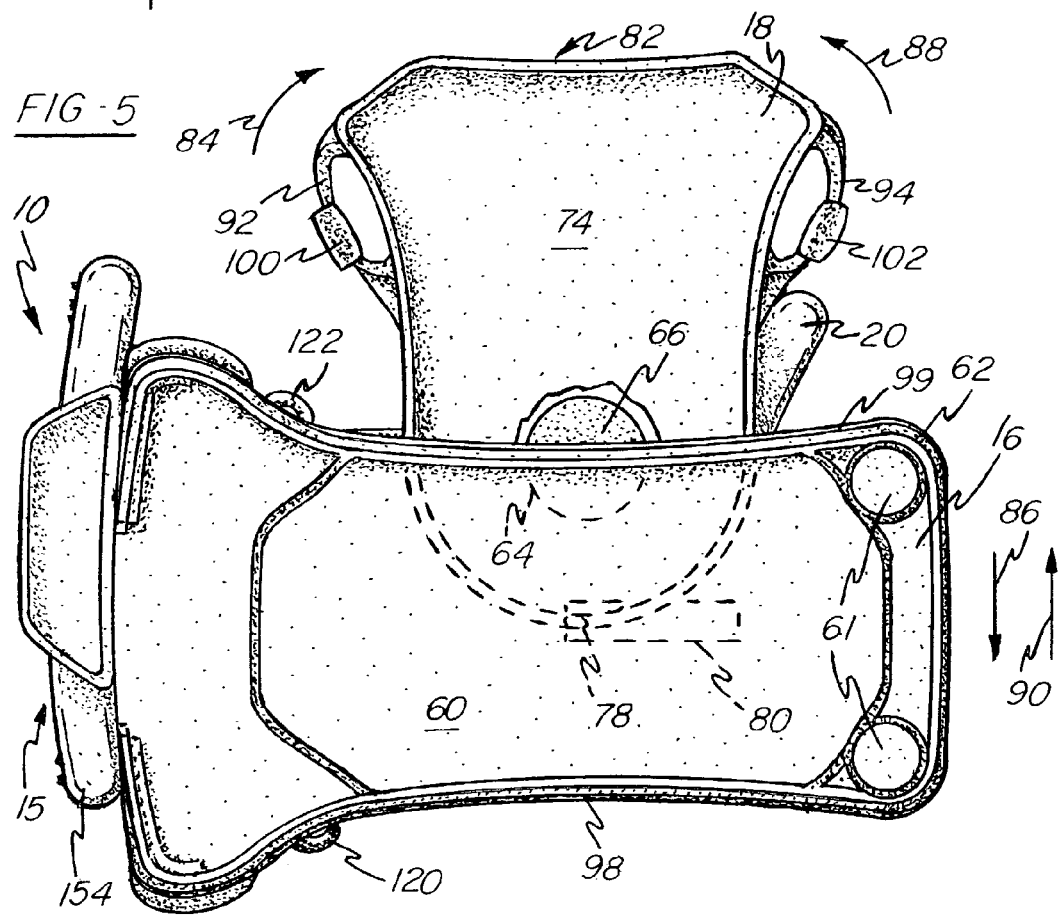

OVERBED TABLE FOR USE WITH A PATIENT SUPPORT

CROSS-REFERENCE TO RELATED APPLICATIONS

This application is a continuation-in-part of U.S. patent application Ser. No. 09/849,580, filed May 4, 2001, which claims the benefit of U.S. Provisional Patent Application Ser. No. 60/202,283, filed May 5, 2000, and U.S. Provisional Patent Application Ser. No. 60/229,136, filed Aug. 30, 2000, and is a continuation-in-part of U.S. patent application Ser. No. 09/835,002, filed Apr. 13, 2001, which claims the benefit of U.S. Provisional Patent Application Ser. No. 60/251,950, filed Dec. 7, 2000, and further claims the benefit of U.S. Provisional Patent Application Ser. No. 60/310,092, filed Aug. 3, 2001, the disclosures of which are expressly incorporated by reference herein.

BACKGROUND AND SUMMARY OF THE INVENTION

This invention relates generally to overbed tables of the type extending above a patient support surface. More particularly, the invention relates to an overbed table incorporating a display device and/or a camera configured to be used by a patient supported on a hospital bed or by a caregiver located adjacent to the bed.

The present invention provides an overbed table of the type cantilevered over a patient support, such as a hospital bed, and configured to support materials utilized by a patient.

According to an illustrative embodiment of the invention, an overbed table includes a frame coupled to first and second table sections, wherein the second table section is supported in vertically spaced relation to the first table section. A support is positioned in vertical spaced relation to the first table section and is configured to move relative to the first table section within a substantially horizontal plane. A display screen is coupled to the support and is configured to move between a substantially horizontal storage position and a substantially vertical use position.

Illustratively according to the embodiment, at least one of the first table section and the second table section is configured to move in a substantially horizontal plane with respect to the other of the second table section and the first table section. Illustratively, the second table section is coupled to the first table section and the frame such that movement of the second table section results in sliding movement of the first table section.

Further illustratively according to the embodiment, the support comprises an arm having first and second handles, wherein the display screen is supported intermediate the first and second handles.

Illustratively according to the embodiment, the support is pivotably connected to the first table section.

Illustratively according to the embodiment, the display screen is coupled to the support for pivoting movement about a substantially horizontal first axis and for pivoting movement about a second axis extending substantially perpendicular to the first axis.

Further illustratively according to the embodiment, the display screen is located intermediate the first and second table sections in the storage position and extends above the first table section in the use position.

Illustratively according to the embodiment, the display screen comprises one of a flat panel monitor and a reflective mirror.

Illustratively according to the embodiment, a camera is supported proximate the display screen.

Further illustratively according to the embodiment, the first table section is supported by the frame for movement between a generally vertical position and a generally horizontal position.

Further illustratively according to the embodiment, the second table section is releasably coupled to the first table section and the frame permits movement of the first table section between a generally vertical position and a generally horizontal position independently of the second table section.

Illustratively according to the embodiment, the first table section is supported by the frame by an inner member provided on one of the frame and the first table section and an outer member provided on the other of the frame and the first table section, the inner member extending rotatably and slidably through the outer member to permit sliding movement and pivoting movement of the first table section with respect to the frame.

Further illustratively according to the embodiment, a rest is supported by one of the frame and the first table section, the rest configured to support the first table section in the generally horizontal position.

Illustratively according to the embodiment, the frame includes a telescoping support column having an outer column portion and an inner column portion, the telescoping support column supporting the first and second table sections, and a base coupled to the telescoping support column.

Further illustratively according to the embodiment, the second table section is coupled to the first table section by a first pivotal coupling between the first and second table sections.

Illustratively according to the embodiment, the first pivotal coupling includes a first bearing provided on one of the first and second table sections and a bearing race provided on the other of the first and second table sections, the first bearing engaging the bearing race to permit pivoting of the second table section about a first axis with respect to the first table section. The second table section is illustratively coupled to the frame by a second pivotal coupling between the second table section and the frame.

Illustratively according to the embodiment, the second pivotal coupling includes a trunnion provided on one of the frame and the second table section and a recess provided on the other of the frame and the second table section for receiving the trunnion to permit pivoting of the second table section about a second axis with respect to the first table section, the second axis being spaced from the first axis.

Illustratively according to the embodiment, the display screen is coupled to the first table section by a third pivotal coupling connected to the first table section.

Further illustratively according to the embodiment, a processor is provided in communication with the display screen.

Illustratively according to the embodiment, a connector is supported by the frame and is configured to operably connect with a bed frame for placing the display screen in communication with a processor.

According to a further embodiment of the invention, an overbed table includes a frame having a vertically extending support column, a table section supported by the frame and configured to cantilever over a patient support surface including opposing head and foot ends, and a camera supported by the frame and directed toward the head end of the patient support.

Illustratively according to the embodiment, a display screen is supported by the frame and includes a viewable surface directed toward the head end of the patient support surface. The camera is illustratively supported by the display screen.

Further illustratively according to the embodiment, a support is configured to move relative to the table section within a substantially horizontal plane, the display screen being coupled to the support and configured to move between a substantially horizontal storage position and a substantially vertical use position.

Illustratively according to the embodiment, a processor is supported by the frame and is in communication with the camera.

Further illustratively according to the embodiment, a connector is supported by the frame and is configured to operably connect with a bed frame for placing the camera in communication with a remote processor.

Illustratively according to the embodiment, at least one solar cell is supported by the frame and is operably connected to the camera, wherein the at least one solar cell is alignable with a light source connected to the patient support surface.

According to a further illustrative embodiment of the invention, an overbed table includes a frame having a vertically extending support column, and a table section supported by the frame and configured to cantilever over a patient support surface including opposing head and foot ends, and a display device supported by the frame and coupled to a power source. The display device includes first and second sides, and a viewable surface supported by the first side and directed toward the head end of the patient support.

Illustratively according to the embodiment, a camera is supported by the frame and is directed toward the head end of the patient support surface. The camera is provided in communication with the display device, thereby defining an electronic mirror.

Further illustratively according to the embodiment, the camera is supported by the display device.

Illustratively according to the embodiment, a support is configured to move relative to the table section within a substantially horizontal plane, the display device being coupled to the support and configured to move between a substantially horizontal storage position and a substantially vertical use position.

Further illustratively according to the embodiment, a processor is supported by the frame and is in communication with the display device.

Illustratively according to the embodiment, a connector is supported by the frame and is configured to operably connect to a bed frame for placing the display device in communication with a remote processor.

Further illustratively according to the embodiment, at least one solar cell is supported by the frame and is operably connected to the display device, wherein the at least one solar cell is alignable with a light source connected to the patient support surface.

Illustratively according to the embodiment, a reflective mirror is supported by the second side of the display device.

According to another illustrative embodiment of the invention, an overbed table includes a table section having upper and lower surfaces, the table section being configured to cantilever over a patient support surface. The overbed table further includes a support positioned in vertical spaced relation to the table section, at least one of the table section and the support being configured to move relative to the other of the support and the table section, and a monitor coupled to the support and in communication with a power source.

Illustratively according to the embodiment, the monitor is coupled to the support for movement between a storage position below the lower surface of the first table section and a use position extending above the upper surface of the first table section.

Illustratively according to the embodiment, the support comprises an arm pivotally supported below the lower surface of the table section for pivoting movement about a substantially vertical axis.

Further illustratively according to the embodiment, a coupler connects the monitor and the arm, the coupler supporting the monitor for a first pivoting movement about a substantially horizontal axis and for a second pivoting movement about a second axis substantially perpendicular to the first axis.

Further illustratively according to the embodiment, a keyboard is coupled to the support.

Further illustratively according to the embodiment, the support comprises a tray slidably supported below the table section and defining a storage compartment, the monitor being supported by the tray for pivoting movement about a substantially horizontal axis. The monitor is illustratively configured to fold into the storage compartment beneath the table section.

Illustratively according to the embodiment, the monitor is supported by an arm configured to move vertically relative to the table section. The arm illustratively includes a vertical portion, a horizontal portion pivotally connected to the vertical portion, and a coupler connecting the monitor to the horizontal portion. The coupler supports the monitor for a first pivoting movement about a first axis and for a second pivoting movement about a second axis disposed substantially perpendicular to the first axis.

According to yet another illustrative embodiment of the invention, an overbed table includes a frame, a housing coupled to the frame and defining a storage compartment, and a table section coupled to the housing. The table section is supported for movement between first and second positions, the first position substantially covering the storage compartment and the second position providing access to the storage compartment. A display screen is coupled to a power source and is removably supported within the storage compartment.

Illustratively according to the embodiment, the display screen is supported by an arm including a vertical portion. The arm illustratively includes a horizontal portion coupled to the vertical portion, and a coupler connects the display screen to the horizontal portion. The coupler supports the display screen for a first pivoting movement about a first axis and for a second pivoting movement about a second axis disposed substantially perpendicular to the first axis.

Illustratively according to the embodiment, a collapsible stand is coupled to the display screen for supporting the display screen on an upper surface of the table section.

Further illustratively according to the embodiment, the display screen comprises a flat panel monitor.

Illustratively according to the embodiment, a processor is in communication with the display screen.

Further illustratively according to the embodiment, a connector is supported by the frame and is configured to operably connect with a bed frame for placing the display screen in communication with a remote processor.

Additional features of the invention will become apparent to those skilled in the art upon consideration of the following detailed description when taken in conjunction with the accompanying drawings.

BRIEF DESCRIPTION OF THE DRAWINGS

The detailed description particularly refers to the accompanying figures in which:

FIG. 3 is a partially exploded perspective view of the overbed table of FIG. 1;

FIG. 4 is a top plan view, with a partial cut-away, of the overbed table of FIG. 1;

FIG. 5 is a top plan view similar to FIG. 4, illustrating the second table section in an open or use position and the display support in a closed or storage position;

DETAILED DESCRIPTION OF THE DRAWINGS

Figure 1:
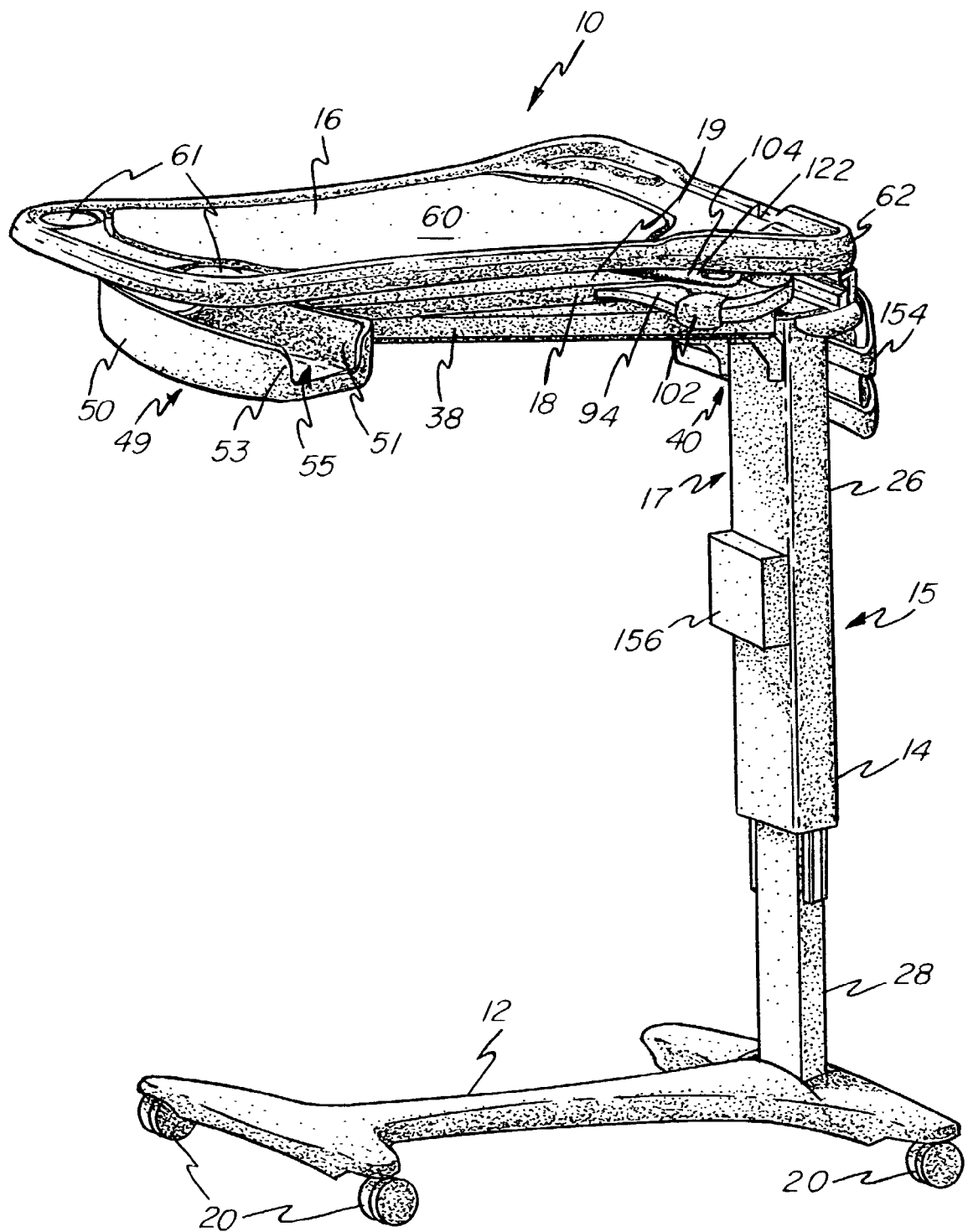
FIG. 1 is a perspective view of an illustrative embodiment overbed table of the present invention, illustrating the second table section and the display support in closed or storage positions.
Figure 2:
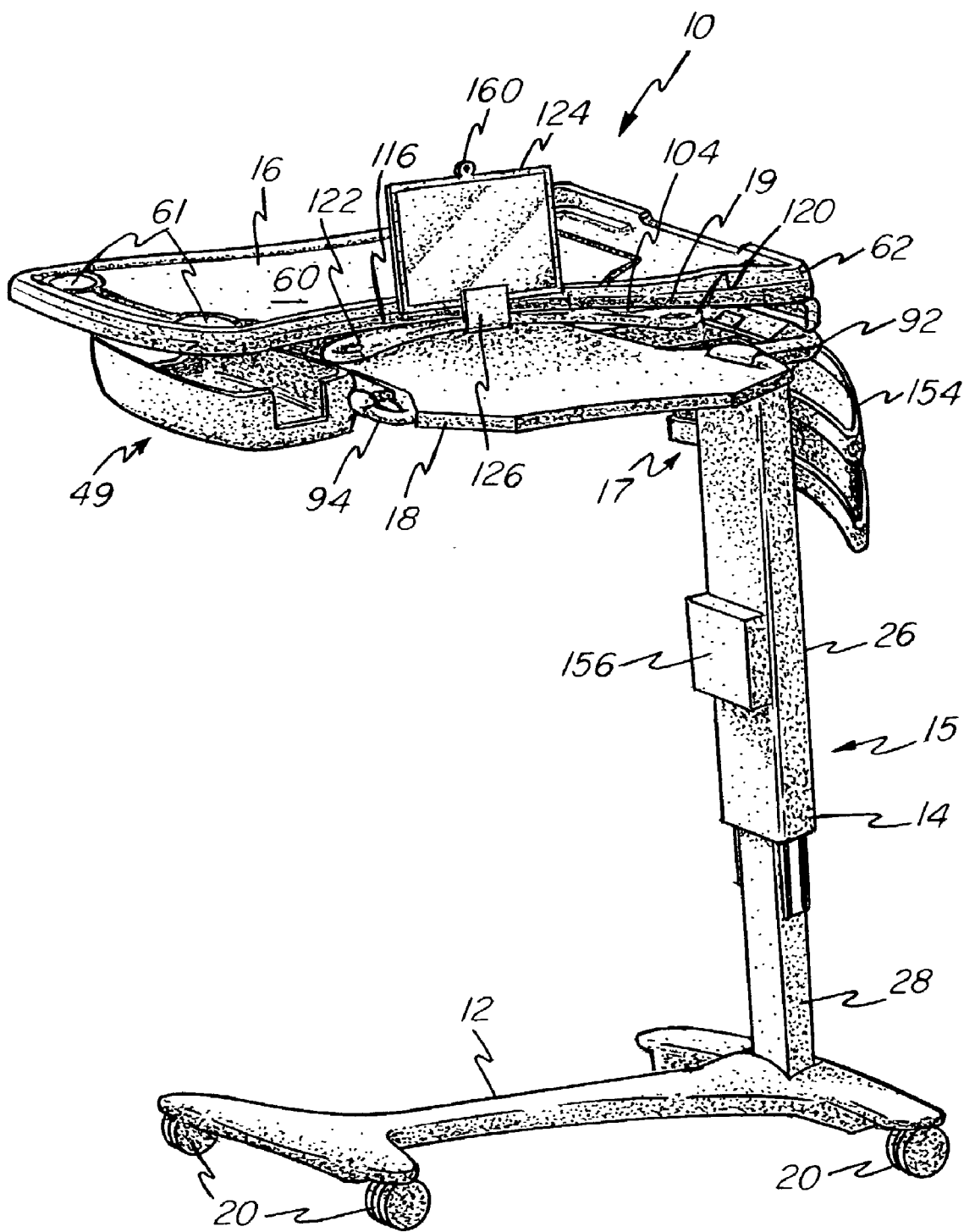
FIG. 2 is a perspective view similar to FIG. 1, illustrating the second table section and the display support in open or use positions.

Referring initially to FIGS. 1–3, an overbed table 10 according to an illustrative embodiment of the present invention includes a base 12 and a telescoping support column 14. The base 12 and the telescoping support column 14 combine to form a frame 15 which supports first and second table sections 16 and 18. In the following description, the first table section 16 may also be referred to as an upper table, and the second table section may also be referred to as a food tray. The first and second table sections 16 and 18 are mounted in vertically spaced relation proximate an upper end 17 of the support column 14. Illustratively, the first table section 16 is positioned in spaced relation above the second table section 18, thereby defining a vertical space or an open region 19 therebetween. The base 12 is generally I-shaped in plan view and is illustratively provided at its four extremities or corners with casters 20 which facilitate the convenient positioning of the overbed table 10.

Figure 23:
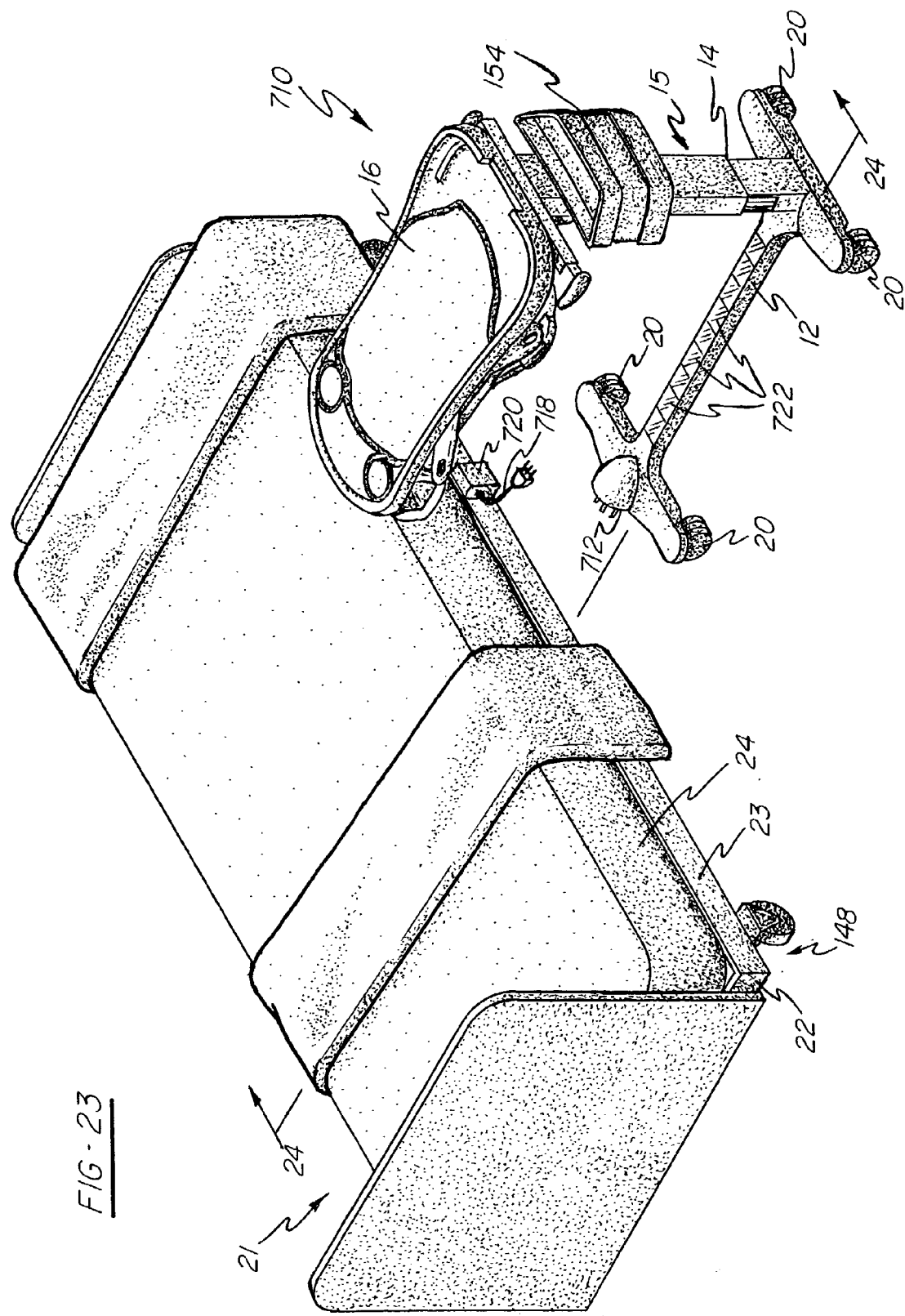
FIG. 23 is a perspective view of a further illustrative embodiment overbed table of the present invention, illustrating a docking connector and a solar power device supported by the base of the frame of the overbed table.
Figure 24:
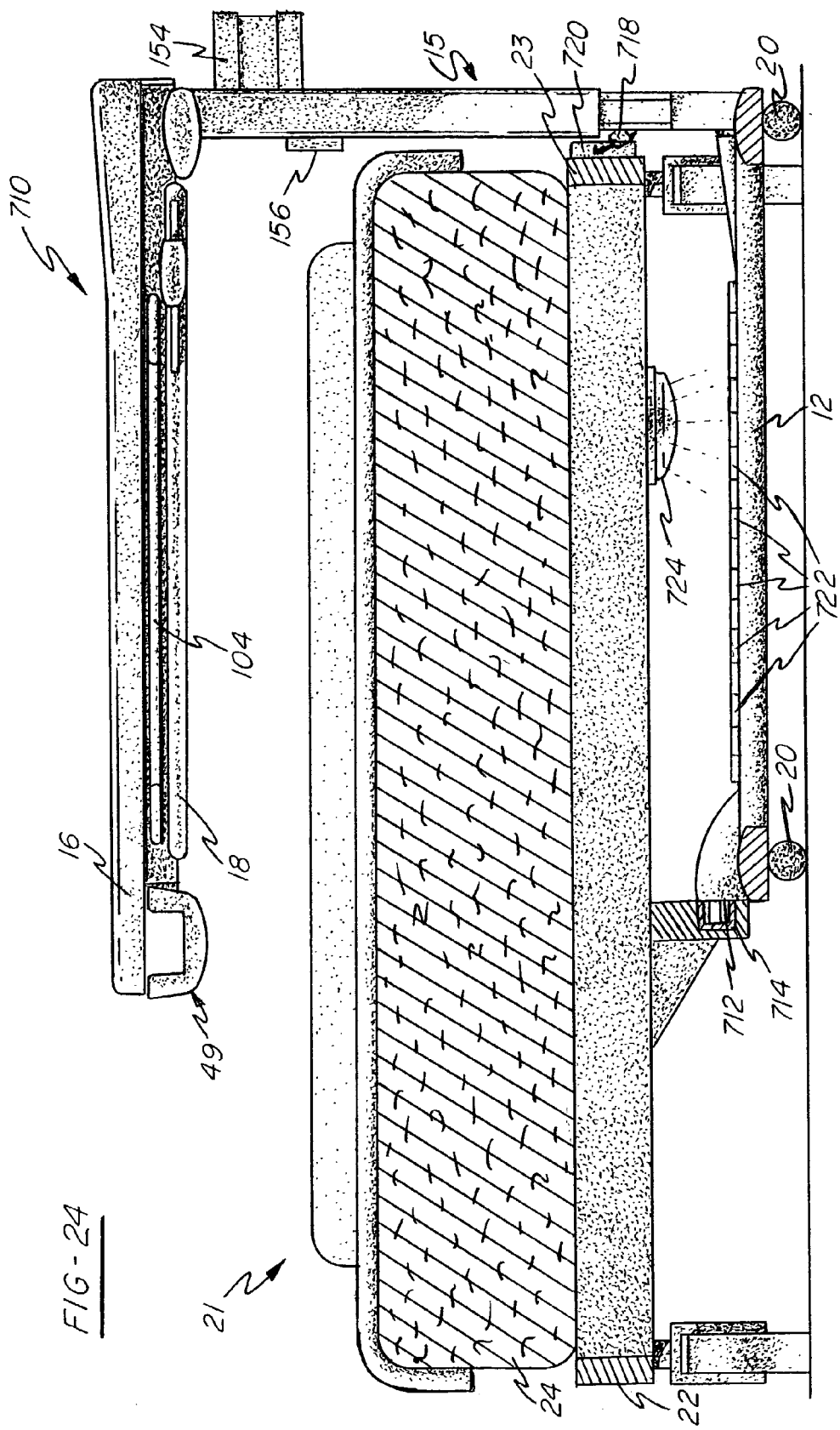
FIG. 24 is a cross-sectional view illustrating the interaction of the overbed table of FIG. 23 when fully docked to a hospital bed.

The telescoping support column 14 illustratively extends upwardly from the base 12 at an angle of, for example, 0° to 10° generally to vertical to facilitate positioning of the overbed table 10 with respect to a conventional bed 21. More particularly, the support column 14 is configured to be positioned adjacent a conventional bed frame 22 including bed rail 23 supporting a mattress 24 (FIGS. 23 and 24).

The support column 14 includes upper and lower telescoping portions 26 and 28, respectively. The upper portion 26 is configured to move in a generally vertical direction relative to the lower portion 28. Additional details of the support column 14 are provided in co-pending patent application Ser. No. 09/835,002, which is assigned to the assignee of the present invention and is expressly incorporated by reference herein.

Referring further to FIGS. 1, 3 and 4, a sleeve 30 is provided proximate the upper end 17 of the support column 14 and extends in a generally horizontal direction. The first table section 16 includes a rod or tube 32 having substantially the same cross-section transverse to its longitudinal axis as an interior channel 34 of the sleeve 30 (FIG. 3). The rod or tube 32 extends through the sleeve 30 and is slidably and rotatably movable about its longitudinal axis 36 within the sleeve 30, as illustrated in FIGS. 3, 4, 5, and 7 to permit the first table section 16 to slide linearly away from the second table section 18 and to rotate between a generally upright vertical position and a horizontal table position.

Adjacent its upper end 17, the support column 14, as illustrated best in FIGS. 1 and 3, is also provided with a beam 38 which forms a portion of the frame 15. A proximal end 40 of the beam 38 is mounted to the support column 14 and an opposite distal or remote end 42 extends from the support column 14 in a direction generally parallel to the base 12. As such, it may be appreciated that the first table section 16 is supported in a manner such that it cantilevers out from the support column 14. The remote end 42 of the beam 38 is provided with a rest 44 which limits the downward pivoting of the first table section 16 as the rod or tube 32 pivots within sleeve 30. An underside or lower surface 46 of the first table section 16 may include a bearing surface 48 which slides on the rest 44 to reduce wear on the lower surface 46 of the table section 16. A conventional latch (not shown) may be provided to releasably secure the table section 16 to the beam 38.

Referring now to FIGS. 1–3 and 7, a storage tray or bin 49 is illustratively supported by the remote end 42 of the beam 38. The storage bin 49 includes a pair of side walls 50 and 51 and a pair of end walls 52 and 53 connected to a bottom wall 54. The end walls 52 and 53 have notches 55 formed therein to facilitate access to the storage bin 49 when the first table section 16 is positioned thereabove. A mounting tab 56 is connected to the side wall 51 and is secured to the remote end 42 of the beam 38 through a conventional fastener, such as a bolt 57 threadably received by a nut 58.

An upper surface 60 of the first table section 16 may include a plurality of recesses 61 adapted to receive and secure conventional objects that may be used by a person supported on the bed 21 or by a caregiver located adjacent to the bed 21, such as cups and plates (not shown). Additionally a bumper 62 may be secured around a peripheral edge of the first table section 16 in order to protect surfaces which may come in contact with the overbed table 10. The bumper 62 is preferably formed from a resilient material, such as an elastomer or thermoplastic.

As shown in FIG. 3, the second table section 18 includes a lower surface 63 an upper bearing 64 which is generally circular in plan view and provides a generally flat bearing surface. Intermediate the proximal end 40, adjacent the support column 14, and the distal end 42, the beam 38 is provided with a complementary lower bearing surface 66 which is also generally flat and circular. One of the second table section 18 and the beam 38 (beam 38 in the illustrated embodiment) is provided with a pivot post 68, and the other of the second table section 18 and the beam 38 (second table section 18 in the illustrated embodiment) is provided with a recess 70 for receiving the pivot post 68. The second table section 18 is releasably mounted and moves pivotally about pivot axis 72 on the pivot post 68.

On its upwardly facing surface 74 at its distal end 76 remote from the support column 14, the second table section 18 is provided with a roller bearing 78. The lower surface 46 of the first table section 16 includes a bearing track 80 for receiving the roller bearing 78 when the first table section 16 is in its lowered position resting on the rest 44. With this linkage, pivotal movement of the second table section 18 within a horizontal plane results in sliding movement of the first table section 16 along sleeve 30 in a second, parallel horizontal plane. As illustrated in FIGS. 4 and 5, pivotal movement of the proximal end 82 of the second table section 18 away from the support column 14 of the frame 15 in the direction of arrow 84 results in sliding movement of the first table section 16 in a generally opposite direction as represented by arrow 86 (FIG. 5). Pivotal movement of end 82 of second table section 18 toward outer support column 14 of frame 15 in the direction of arrow 88 results in sliding movement of the first table section 16 in a direction generally toward the second table section 18 as represented by arrow 90.

Similarly, sliding movement of the first table section 16 away from the second table section 18 in the direction of arrow 86 results in pivotal movement of the end 82 of the second table section 18 generally away from the support column 14 in the direction of arrow 84. Sliding movement of first table section 16 toward the support column 14 in the direction of arrow 90 results in pivotal movement of the end 72 of the second table section 18 toward the support column 14 and the first table section 16 in the direction of arrow 88.

Generally, it will be understood that horizontal movement in one plane of one table section 16, 18 results in similar horizontal movement in an adjacent, substantially parallel plane of the other table section 16, 18. In a storage position, as illustrated in FIG. 4, the second table section 18 is positioned below the first table section 16. In the use position, as illustrated in FIGS. 5 and 6, the second table section 18 is moved at least partially out from under the first table section 16.

The second table section 18 illustratively includes a pair of handles 92 and 94 positioned proximate opposing longitudinal side edges 96 and 97 thereof to facilitate pivoting movement of the second table section 18 about the pivot post 68. The handles 92 and 94 are configured to extend outwardly from beneath opposing side edges 98 and 99 of the first table section 16. Each handle 92 and 94 may include a gripping portion 100 and 102 to be utilized by a patient in deploying the second table section 18 from the storage position (FIG. 4) to the use position (FIG. 5). The gripping portions 100 and 102 are illustratively formed from a high friction resilient material such as an elastomer.

Figure 6:
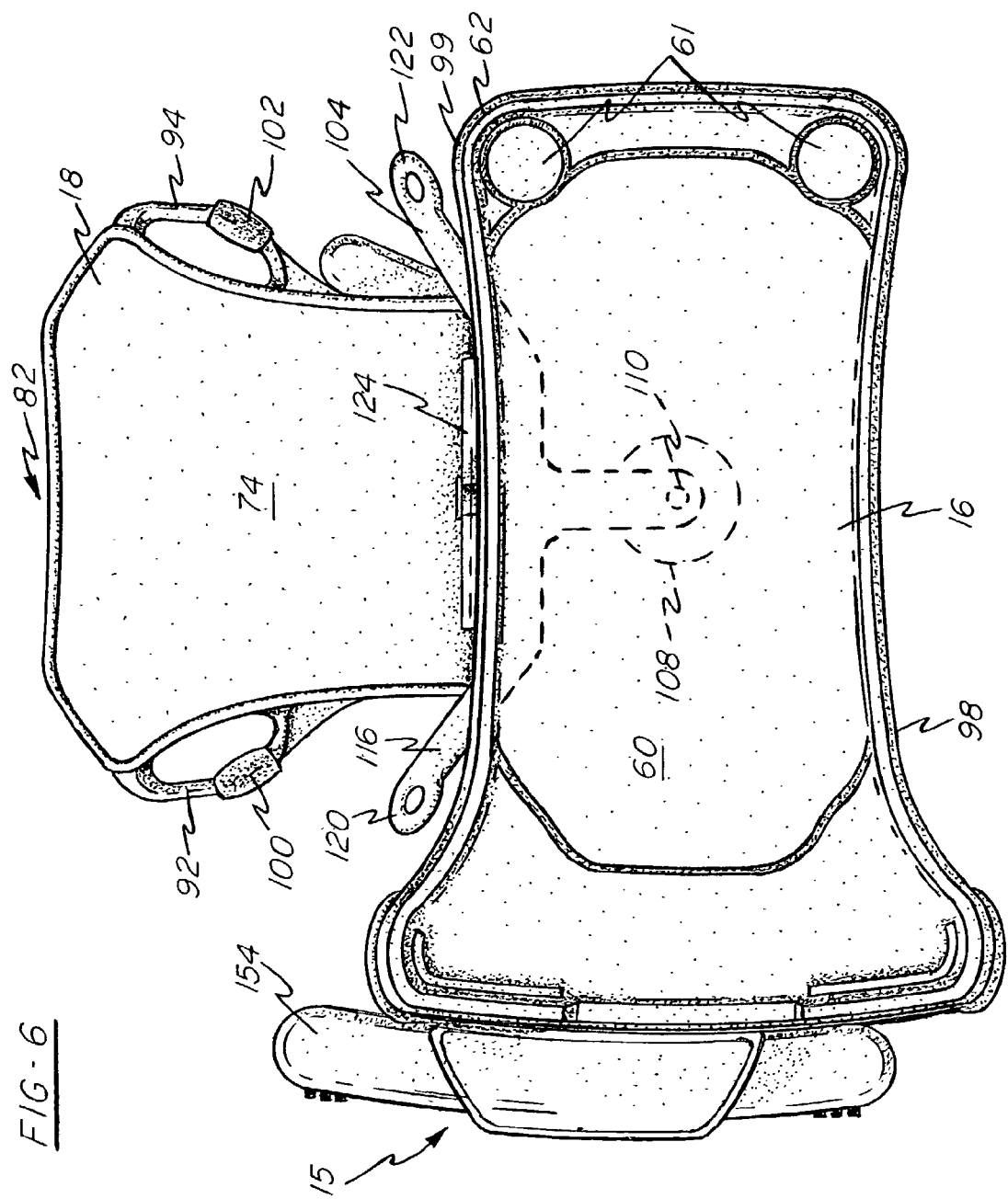
FIG. 6 is a top plan view similar to FIG. 4, illustrating the second table section and the display support in open or use positions.
Figure 7:
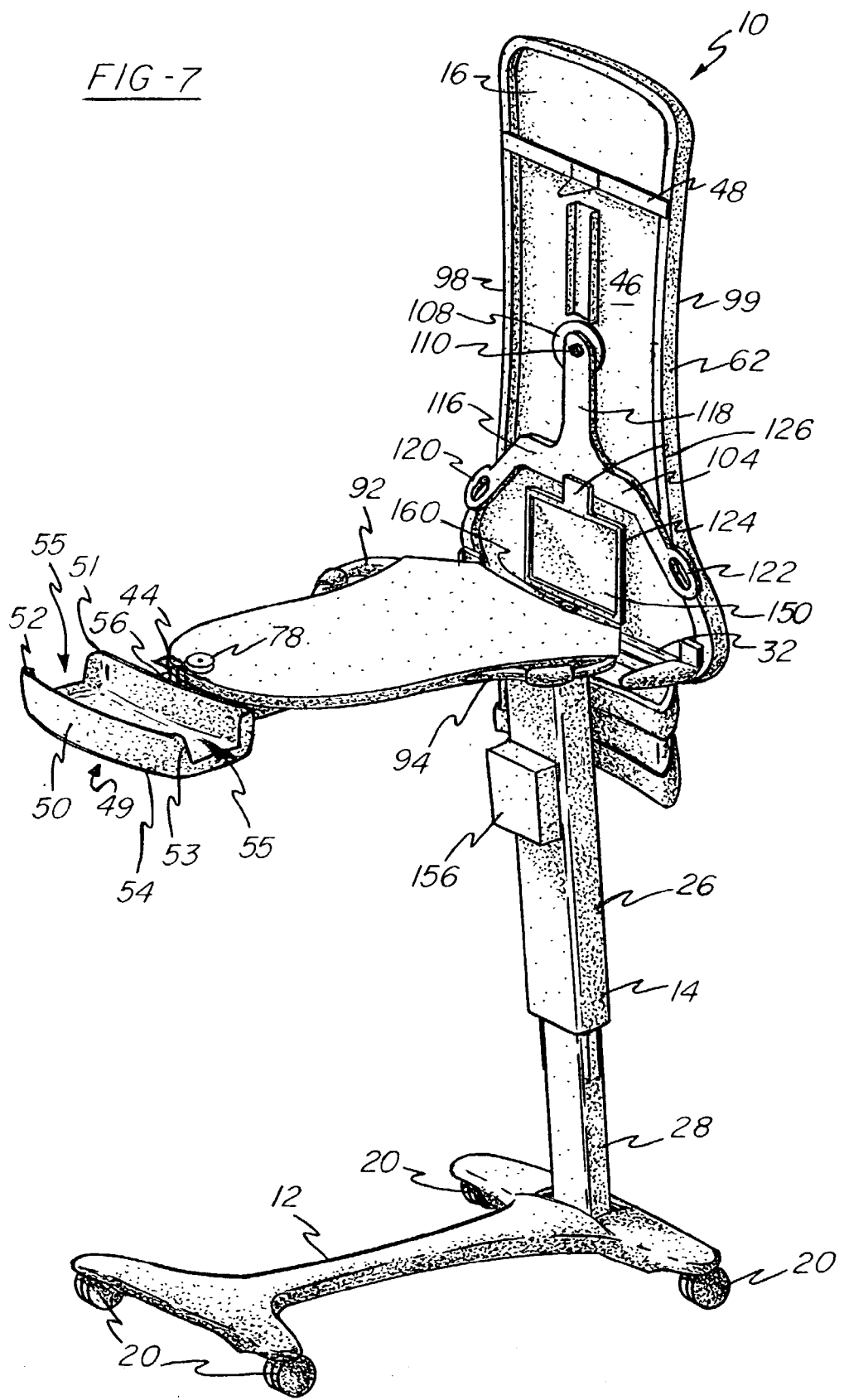
FIG. 7 is a perspective view of the overbed table of FIG. 1 illustrating the first table section in an upright or cleaning position.

With reference to FIGS. 2–4 and 6–8, a support arm 104 is supported within the open region 19 in vertically spaced relation to both the first and second table sections 16 and 18. More particularly, the arm 104 is positioned intermediate, or sandwiched between, the first and second table sections 16 and 18. The arm 104 is supported for pivoting movement within a substantially horizontal plane about a pivot axis 106 (FIG. 3). The lower surface 46 of the first table section 16 illustratively includes a bearing 108 which is generally circular in plan view and provides a generally flat bearing surface for the arm 104. A pivot post 110 is received within a recess 112 formed within the bearing 108. The pivot post 110 may comprise a conventional fastener passing through an opening 114 formed within the arm 104 and threadably received within the recess 112. The arm 104 moves pivotally about the pivot post 110, and hence the pivot axis 106, between a storage position (FIGS. 4 and 5) and a use position (FIG. 6).

The arm 104 illustratively includes a substantially U-shaped portion 116 and a connecting portion 118. The U-shaped portion 116 supports a pair of handles 120 and 122 to facilitate pivoting movement of the arm 104 by a patient. The handles 120 and 122 are configured to extend outwardly from beneath the opposing side edges 98 and 99 of the first table section 16. A display screen or device 124 is supported by the U-shaped portion 116 of the arm 104 by a coupler 126.

Figure 8:
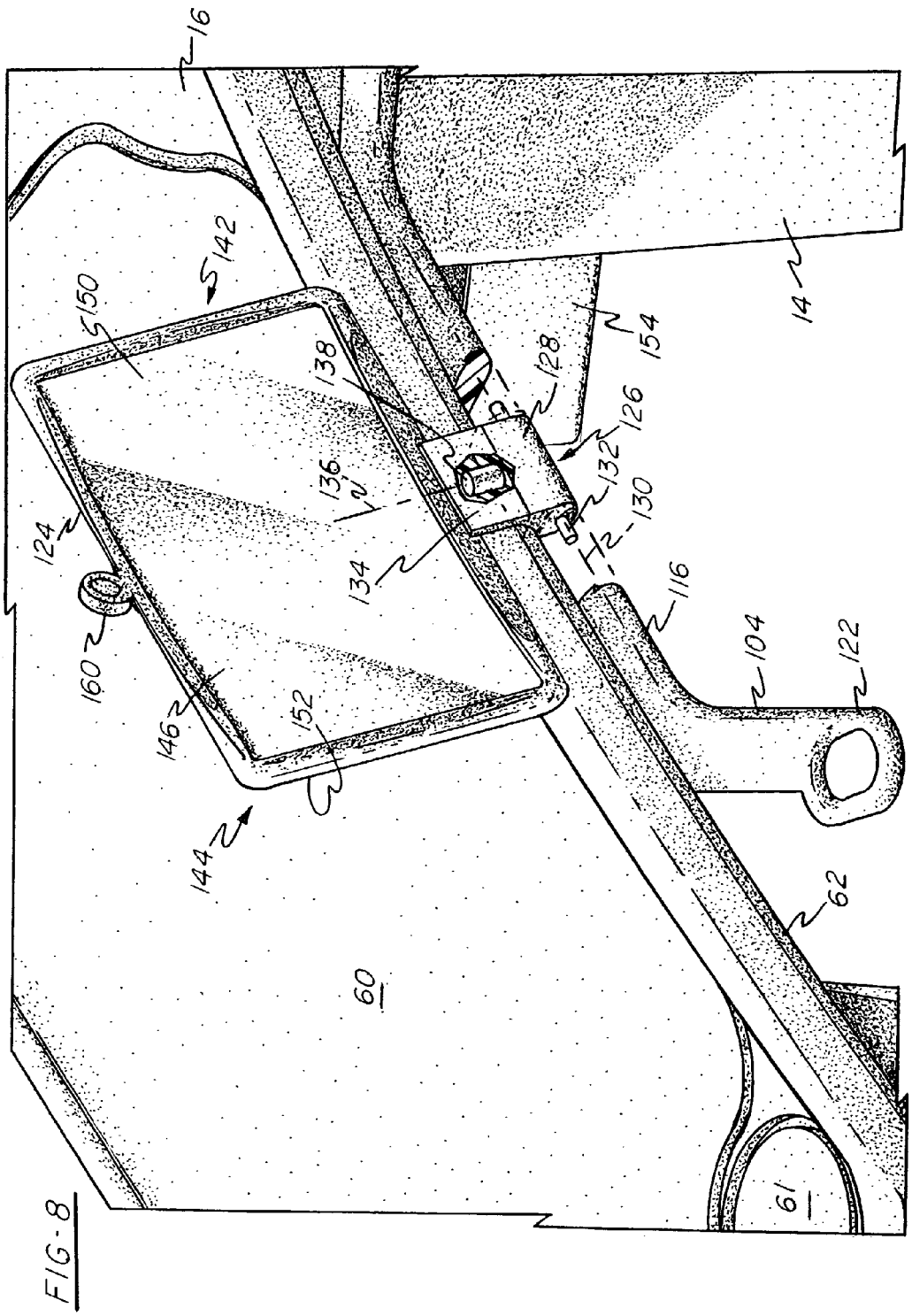
FIG. 8 is a detailed perspective view of the overbed table, with a partial cut-away of the display coupler.

With reference to FIG. 8, the coupler 126 includes a first body portion 128 supported for pivoting movement about a substantially horizontal first pivot axis 130. A first pin 132 couples the first body portion 128 to the U-shaped portion 116 of the arm 104. A second body portion 134 is supported by the first body portion 128 for pivoting movement about a second pivot axis 136 disposed substantially perpendicular to the first pivot axis 130. A second pin 138 couples the second body portion 134 to the first body portion 128. In turn, the display device 124 is fixed to the second body portion 134.

The display device 124 includes first and second sides 142 and 144, with the first side 142 supporting a viewable surface 146 and configured to face toward a head end 148 of the bed 21 (FIG. 23). The display device 124 illustratively comprises a conventional computer monitor wherein the viewable surface 146 comprises an electronic display 150 (FIG. 8). A conventional mirror 152 may be supported by the second side 144 of the display device 124 (FIG. 4). As may be appreciated, the user may alternatively use the electronic display 150 and the mirror 152 by simply rotating the display device 124 about the second pivot axis 136 by moving the second body portion 134 around the second pin 138. In an illustrated embodiment, the display device 124 comprises a flat panel monitor and the electronic display 150 comprises a high resolution liquid crystal display. The viewable surface 146 of the display device 124 may be defined by other conventional screens including, but not limited to, a television screen, or a projection screen, or a conventional mirror. If the display 150 comprises a projection screen, then images may be projected from a remote location onto the viewable surface 146. More particularly, a conventional projector (not shown) may be supported by a structure (such as a ceiling) remote from the overbed table 10 and is configured to project information onto the viewable surface 146.

A processor 154 is supported by the frame 15 and most preferably is fixed proximate the upper end 17 of the support column 14. The processor 154 is in communication with the display device 124 through conventional transmission means, which may include wires or wireless transmitter and receiver (not shown). A power source in the form of a battery 156 may likewise be secured proximate an upper end 17 of the support column 14 and is in communication with the display device 124. It should be appreciated that both the processor 154 and the battery 156 may be located remote from the overbed table 10 wherein communication means are provided in order for the display device 124 to interact with the processor 154 and the battery 156, such as detailed below.

A camera 160, such as a video or digital still image camera, is illustratively supported by the display device 124. The camera 160 is in communication with the processor 154 and may have power supplied by the battery 156. In one illustrative embodiment, the camera 160 provides images to the processor 154 which are then transmitted to the electronic display 150. As such, the electronic display 150, the processor 154, and the camera 160 define an electronic mirror. In other words, the patient facing the camera 160 will see his or her image electronically generated in the electronic display 150.

Figure 9:
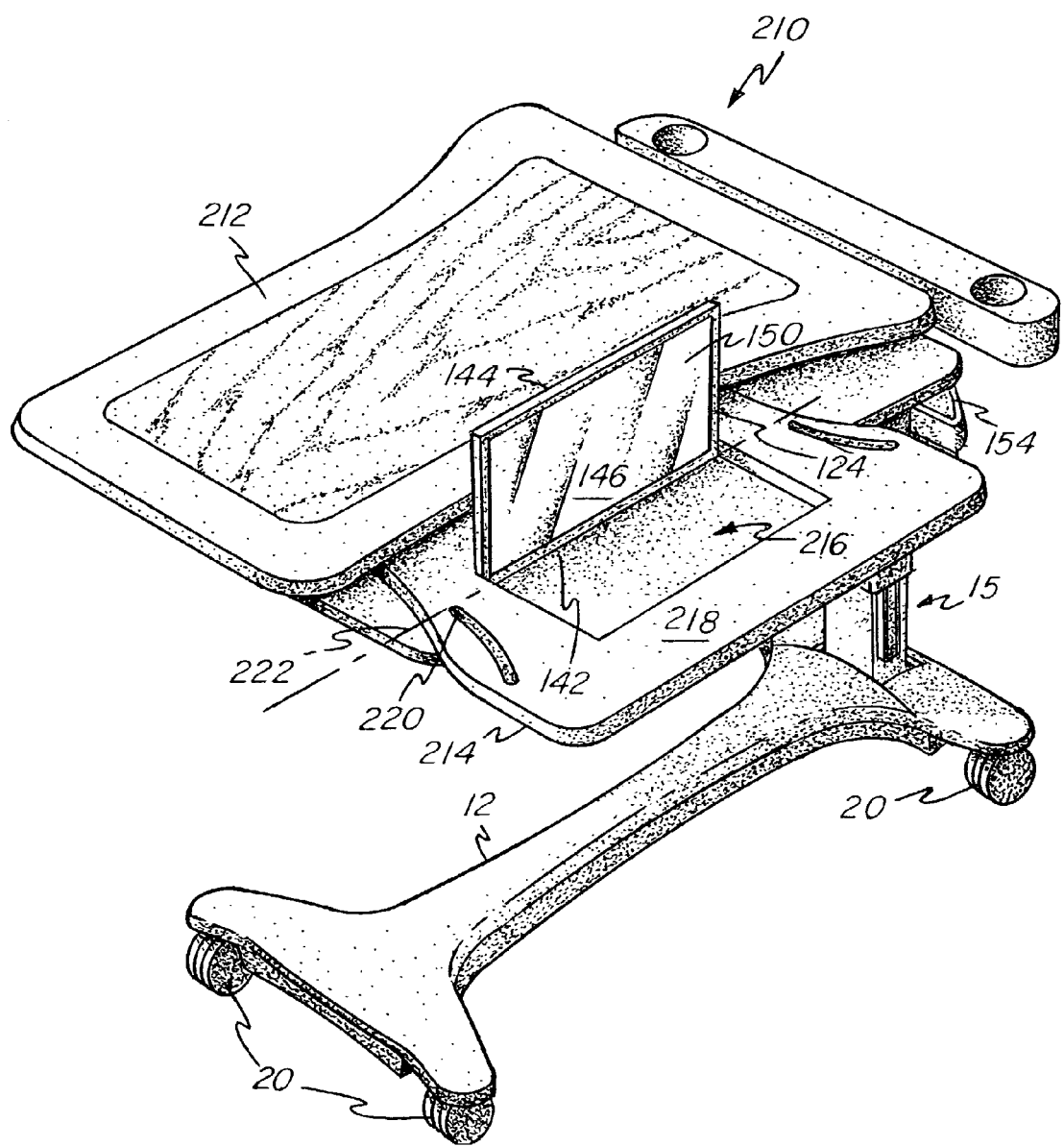
FIG. 9 is a perspective view of a further illustrative embodiment overbed table of the present invention, illustrating the second table section and the display screen in open positions.
Figure 10:
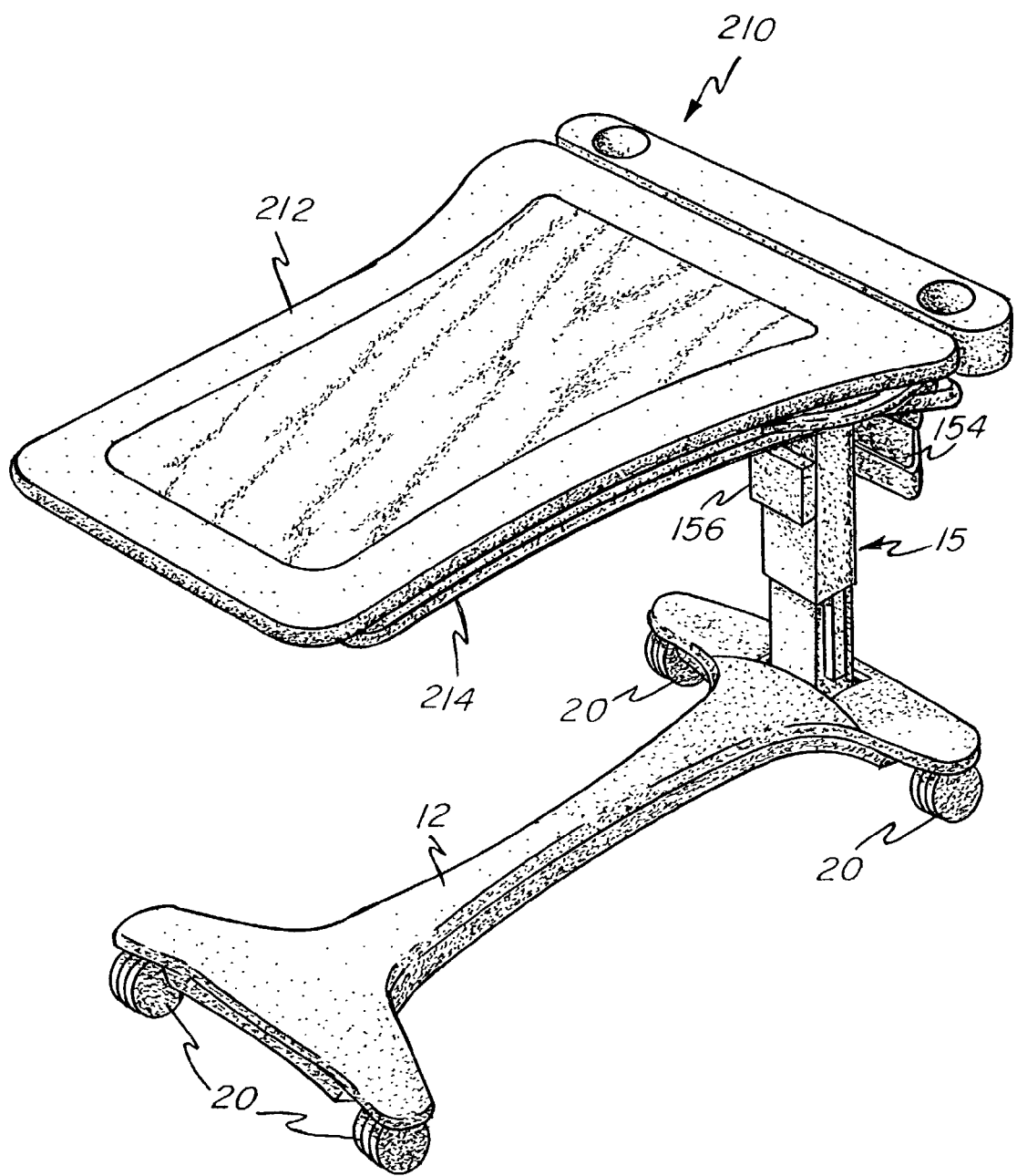
FIG. 10 is a perspective view similar to FIG. 9, illustrating the second table section in a closed position.

A further illustrative embodiment of an overbed table 210 is shown in FIGS. 9 and 10. The overbed table 210 illustratively includes a first table section 212 positioned in vertical spaced relation above a second table section 214. The first table section 212 is supported for sliding movement and the second table section 214 is supported for pivoting movement relative to the first table section 212 in the manner described above with respect to the first table section 16 and the second table section 18 of the illustrative embodiment overbed table 10.

A recess 216 extends downwardly from an upper surface 218 of the second table section 214. The display device 124 is supported by the second table section 214 illustratively through a hinge 220 for pivoting movement about a substantially horizontal pivot axis 222. The display device 124 is adapted to pivot about the pivot axis 222 defined by the hinge 220 between a substantially upright use position (FIG. 9) and a substantially horizontal storage position (FIG. 10). In the storage position, the display device 124 is received within the recess 216 such that the rear or second side 144 of the display device 124 is substantially flush with the upper surface 218 of the second table section 214. In the embodiment of FIGS. 9 and 10, no separate support arm is required for the display device 124.

Figure 11:
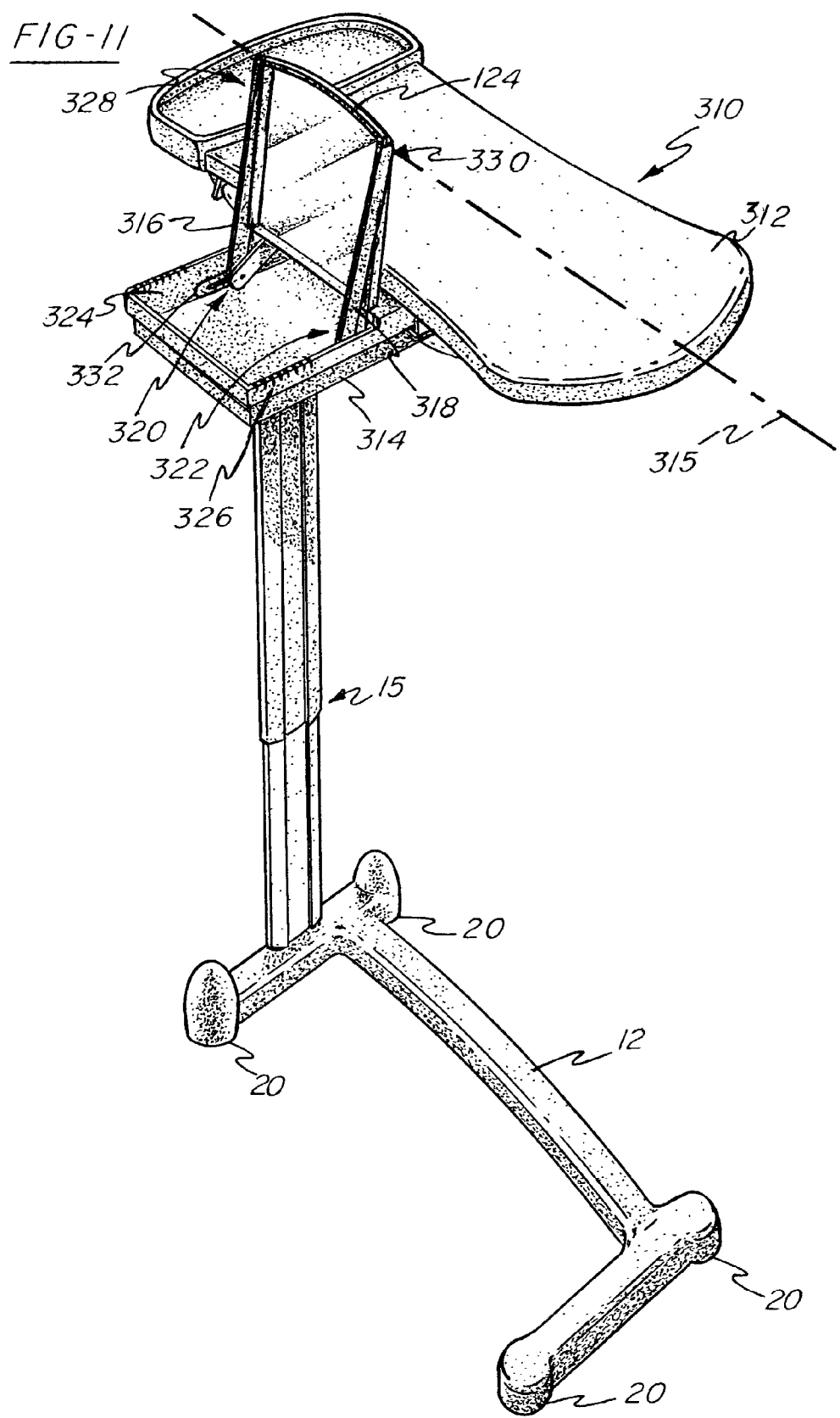
FIG. 11 is a perspective view of yet another illustrative embodiment overbed table of the present invention, illustrating the first table section and the display screen in open positions.
Figure 12:
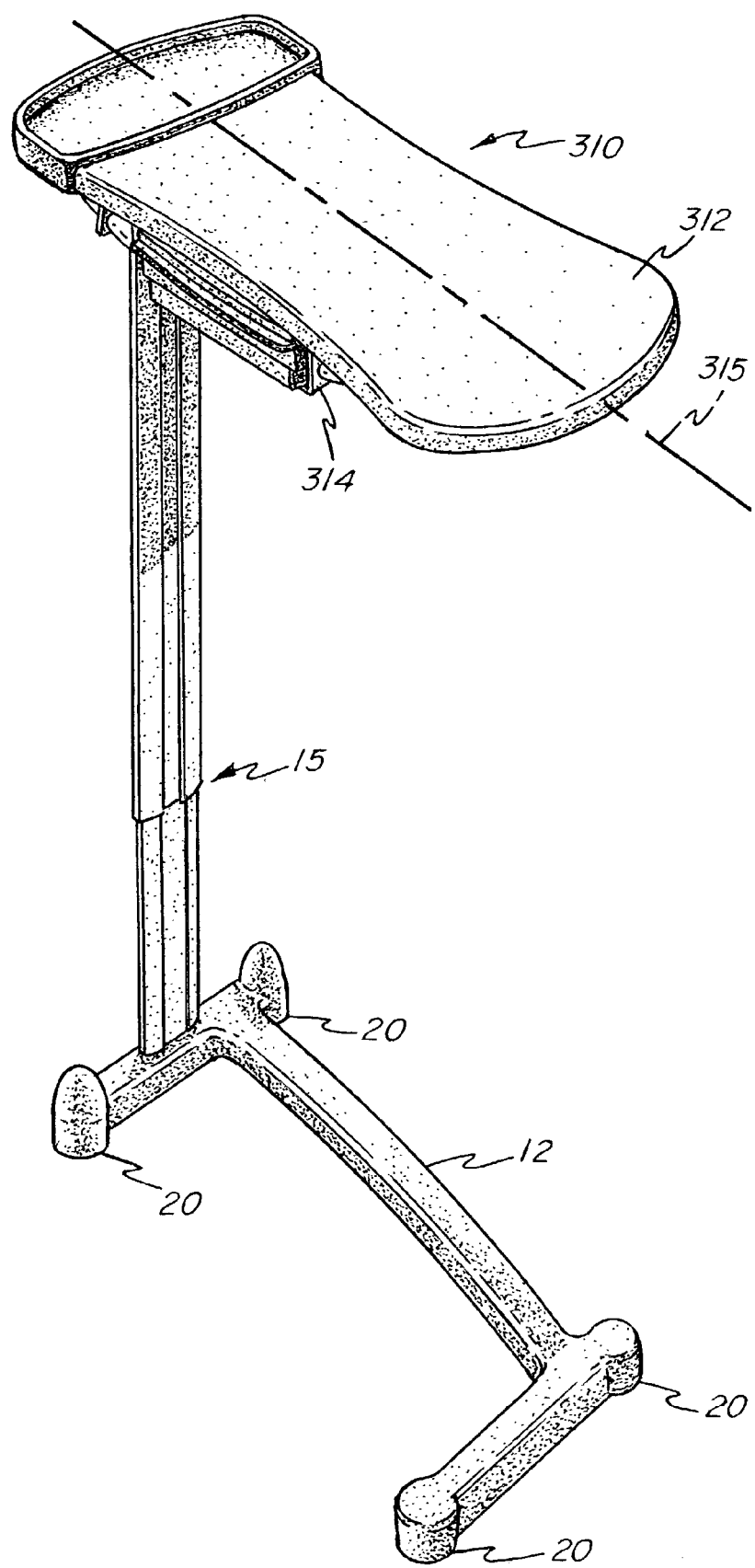
FIG. 12 is a perspective view similar to FIG. 11, illustrating the first table section in a closed position.
Figure 13:
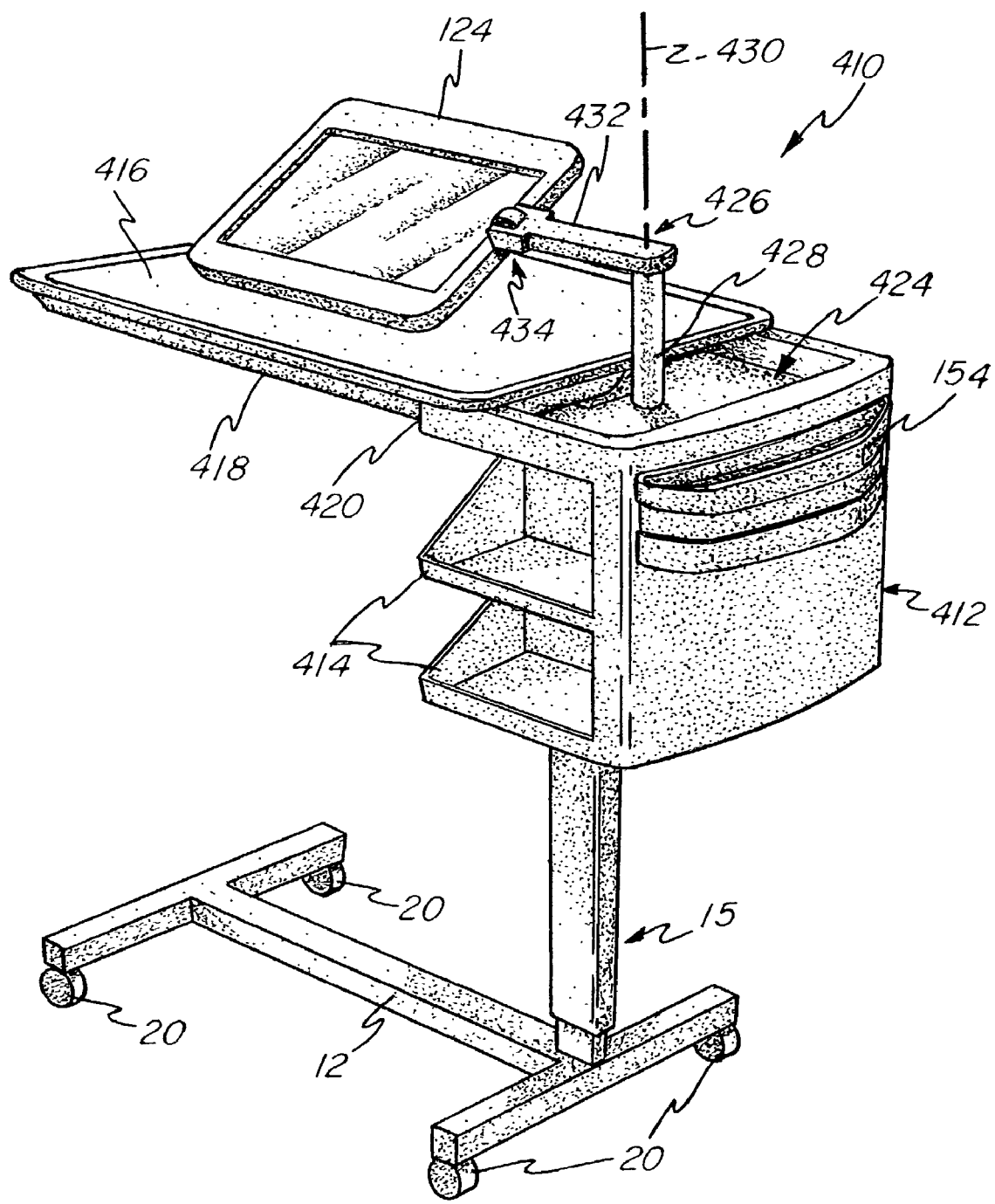
FIG. 13 is a perspective view of a further illustrative embodiment overbed table of the present invention, illustrating the display screen in a fully deployed or use mode of operation.

Turning now to FIGS. 11 and 12, a further embodiment overbed table 310 including a frame 15 supporting a first table section 312. A storage tray 314 is supported in vertical spaced relation below the first table section 312 and is configured to move within a substantially horizontal plane in a direction generally perpendicular to a longitudinal axis 315 of the first table section 312. The display device 124 is coupled to first and second spaced apart arms 316 and 318 which provide for pivoting movement of the display device 124 from an open or use position where the display device 124 is extending upwardly out of the storage tray 314 (FIG. 11) to a closed or storage position where the display device 124 is received within the storage tray 314 below the horizontal plane defined by the first table section 312 (FIG. 12). As illustrated in FIG. 11, first ends 320 and 322 of the arms 316 and 318 are pivotally connected to longitudinally extending side walls 324 and 326 of the storage tray 314, while opposing second ends 328 and 330 of the arms 316 and 318 are pivotally connected to an upper portion of the display device 124. The first ends 320 and 322 of the arms 316 and 318 may be slidably received with channels 332 extending within the side walls 324 and 326 to facilitate folding of the display device 124 into the storage tray 314.

In operation, the display device 124 may be moved between an open position (FIG. 11) and a closed position (FIG. 12) by folding the arms 320 and 322 downwardly into the storage tray 314 such that the display device 124 is nested intermediate the side walls 324 and 326. The storage tray 314 may then be slidably moved in a direction toward the first table section 312 and into the storage position where the storage tray 314 is located in vertically spaced relation immediately below the first table section 312.

Referring now to FIGS. 13–16, a further embodiment of the overbed table 410 of the present invention is illustrated as including a frame 15 supporting a storage unit 412. The storage unit 412 may include a plurality of shelves 414 for use by the patient or a caregiver. It should be appreciated that the shelves 414 may be enclosed by doors (not shown), or replaced with sliding drawers or removable bins (not shown).

Figure 14:
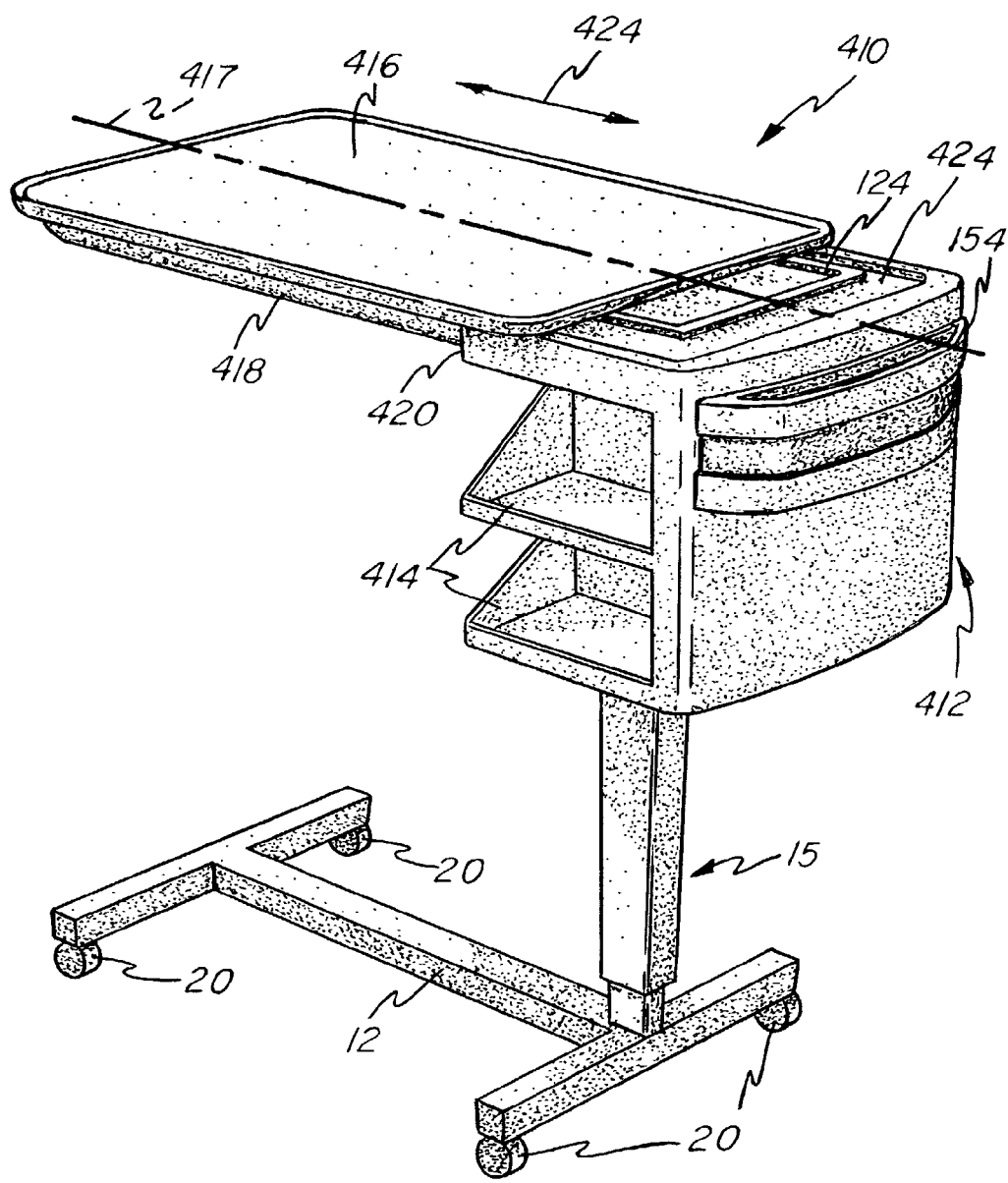
FIG. 14 is a perspective view similar to FIG. 13, illustrating the display screen in a stored mode of operation.
Figure 15:
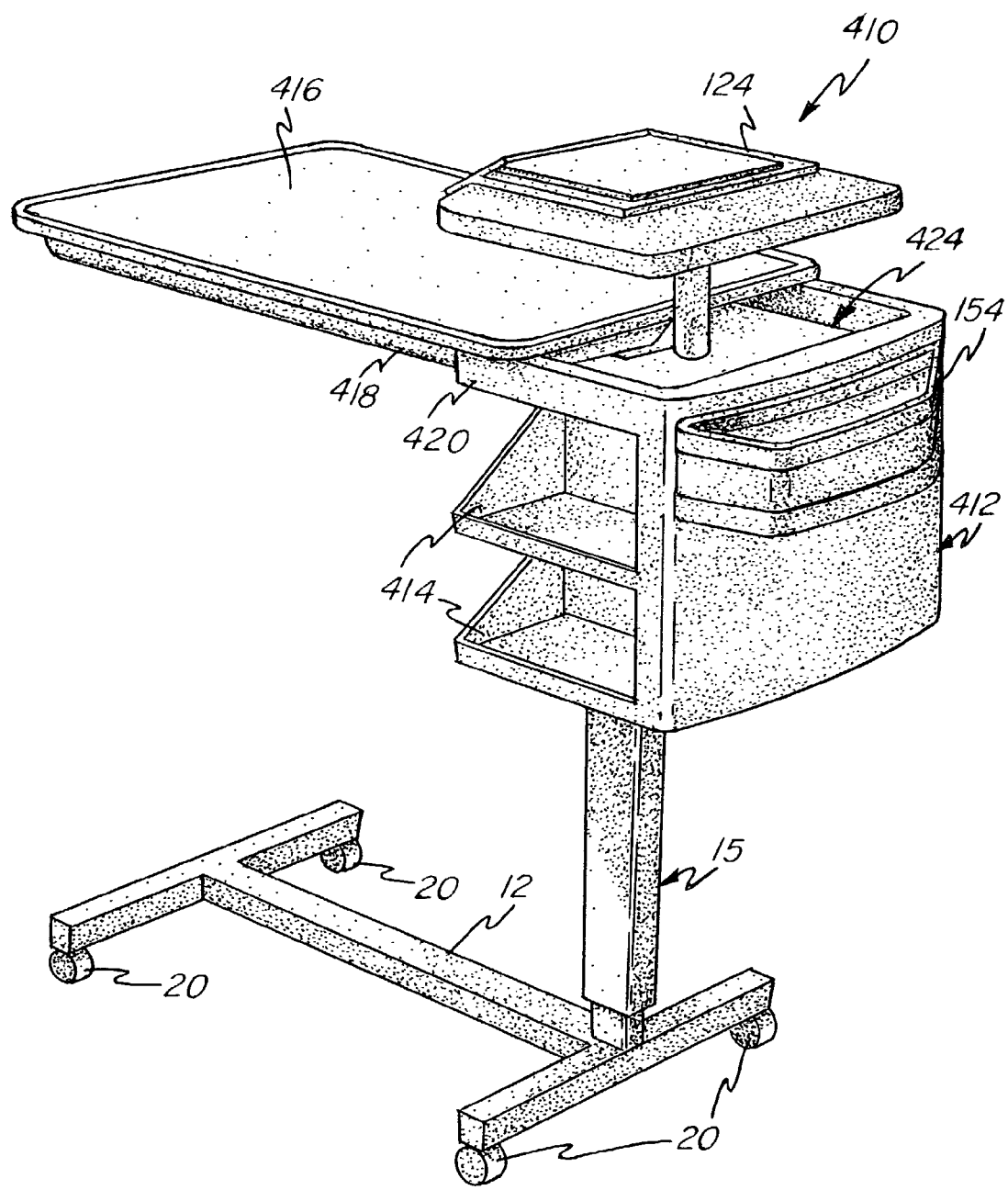
FIG. 15 is a perspective view of the overbed table of FIG. 13, illustrating the display screen in a first partially deployed mode of operation.

A first or upper table section 416 is slidably supported by the storage unit 412 for movement substantially parallel to the longitudinal axis 417 of the first table section 416 (FIG. 14). Moreover, the first table section 416 may include a first or inner guide member 418 supported by the first table section 416, and a second or outer guide member 420 supported by the storage unit 412. As such, the table section 416 may be moved back and forth within a substantially horizontal plane in the direction of double headed arrow 422 to provide access to a storage recess 424 defined by the storage unit 412. The display device 124 is supported within the storage recess 424 when in a storage position (FIG. 14). The display device 124 is supported by an arm 426 configured to move vertically relative to the table section 416. The arm 426 includes a vertical portion 428 supported by the storage unit 412 and pivotable about a substantially vertical axis 430. A horizontal portion 432 is pivotally connected to the vertical portion 428 and a coupler 434 connects the display device 124 to the horizontal portion 432. The coupler 434 supports the display device 124 for a first pivoting movement about a first axis 436 and for second pivoting movement about a second axis 438 which is disposed substantially perpendicular to the first axis 436 (FIG. 16).

Figure 16:
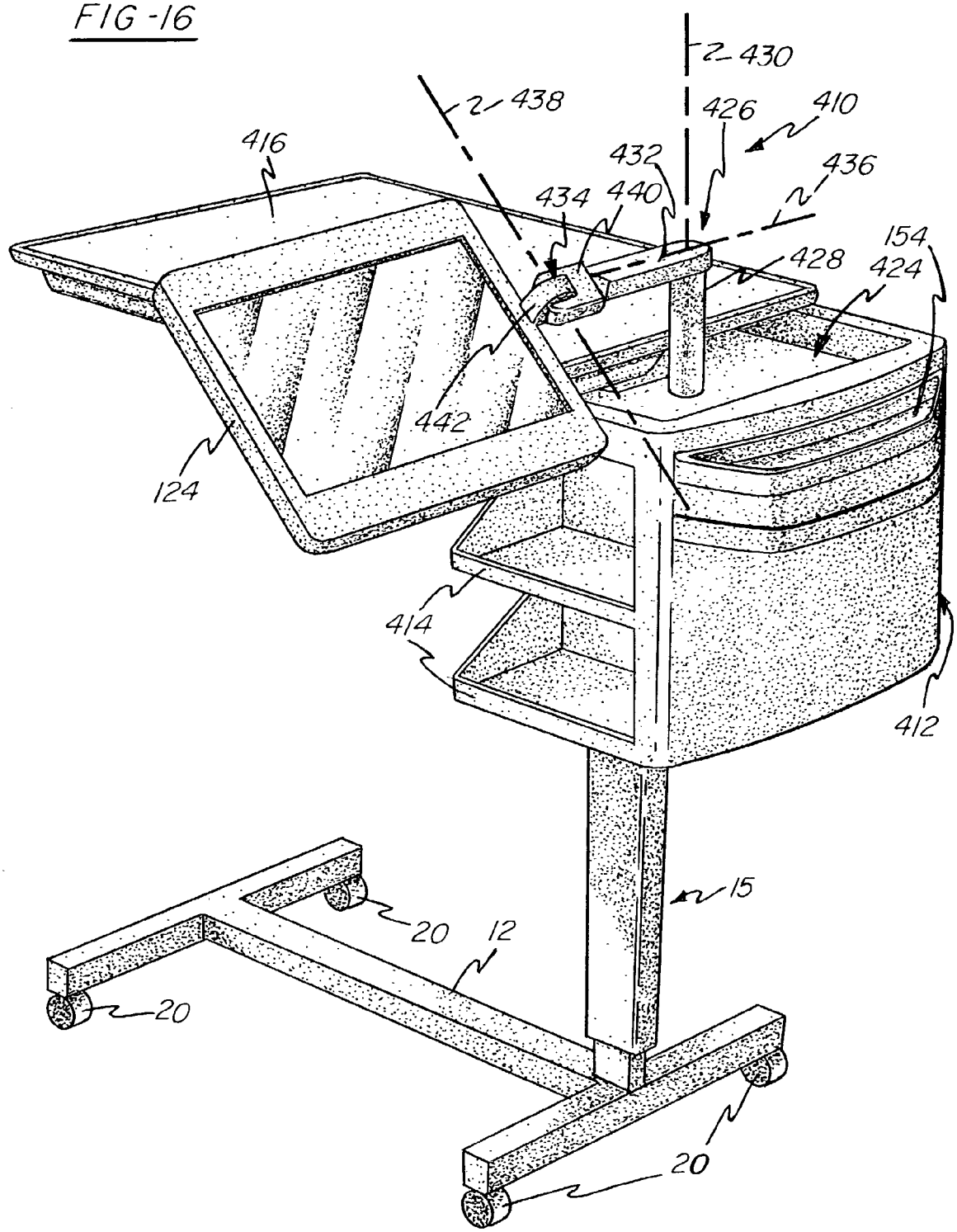
FIG. 16 is a perspective view of the overbed table of FIG. 13, illustrating the display screen in a second partially deployed mode of operation.

Referring further to FIG. 16, the coupler 434 includes a first member 440 rotatable about the first axis 436 and a second member 442 rotatable about the second axis 438. The arm 426 in combination with the coupler 434 provides for movement of the display device 124 into any one of a plurality of different positions as illustrated in FIGS. 13–16.

Figure 17:
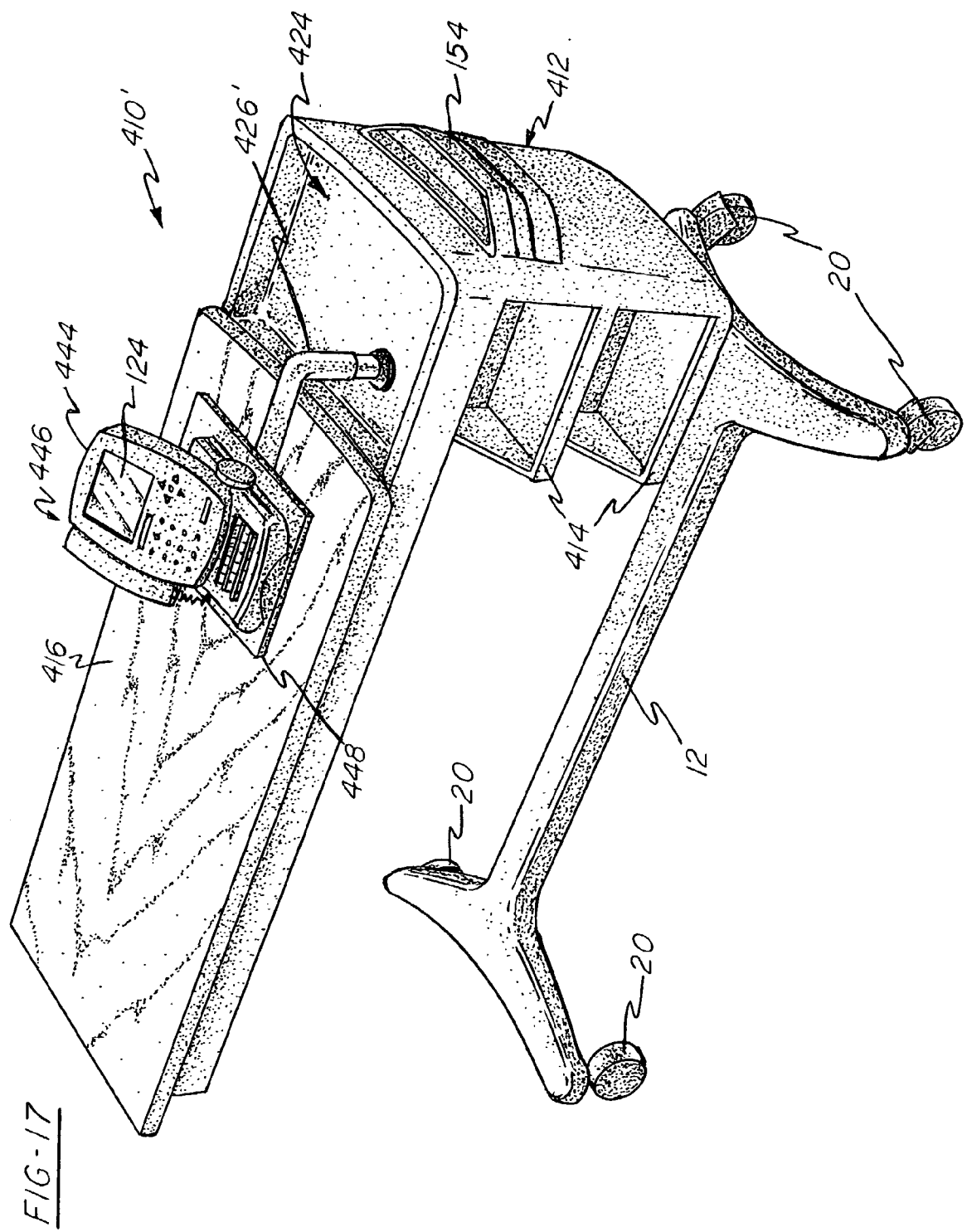
FIG. 17 is a perspective view of a further illustrative embodiment overbed table of the present invention, illustrating the display screen incorporated within a phone and positioned in a fully deployed or use mode of operation.
Figure 18:
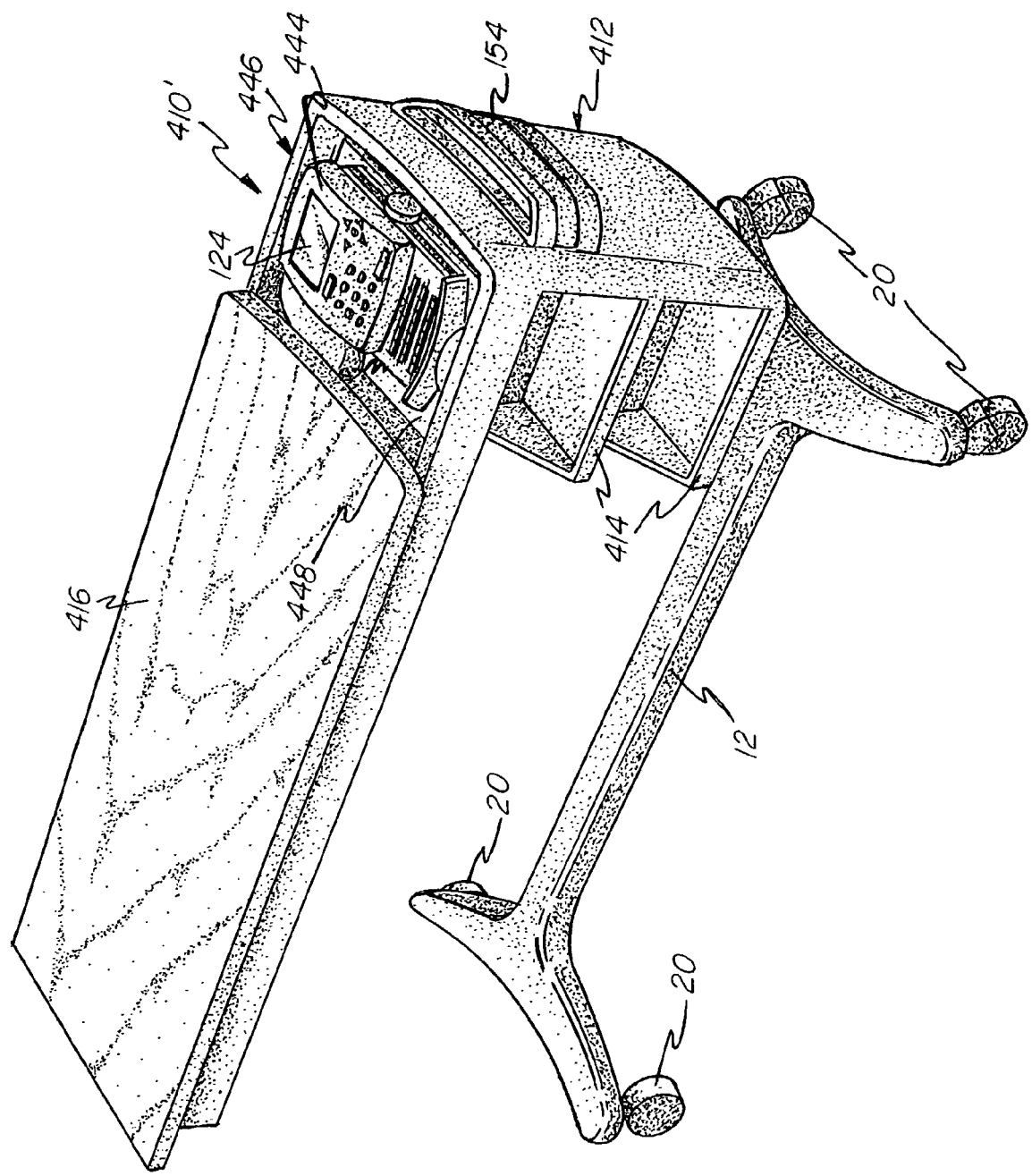
FIG. 18 is a perspective view similar to FIG. 17, illustrating the display screen in a stored mode of operation.

As illustrated in the alternative illustrative embodiment of FIGS. 17 and 18, a communication device, such as a telephone 444 may be supported by the arm 426' adjacent the display device 124. Moreover, the display device 124 and the telephone 444 may be part of an overall computer system 446 coupled to a computer support 448. FIG. 17 illustrates the overbed table 410' in a use position so that the computer system 446 is accessible to a patient. As such, the patient has access to email, the internet, a care plan, or other items such as computer games which are readily accessible through a computer network. The patient may also conduct business or transmit emails to caregivers asking questions. FIG. 18 illustrates the overbed table 410' in a storage position where the computer system 446 is received within the storage recess 424 below the horizontal plane of the table section 416.

Figure 19:
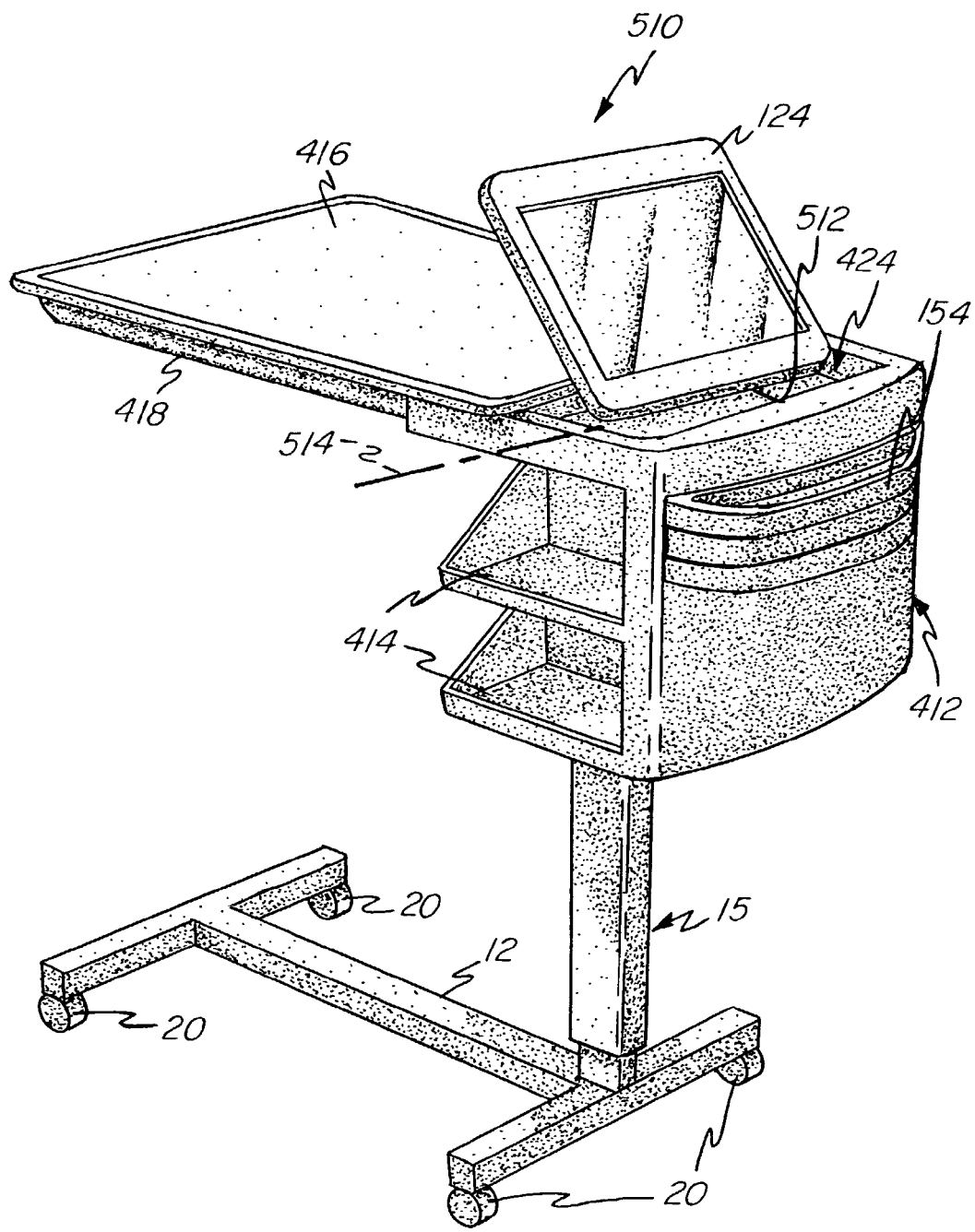
FIG. 19 is a perspective view of a further illustrative embodiment overbed table of the present invention, illustrating a display screen pivotally supported in a storage position within a storage compartment and positioned in a use mode of operation extending above the first table section.
Figure 20:
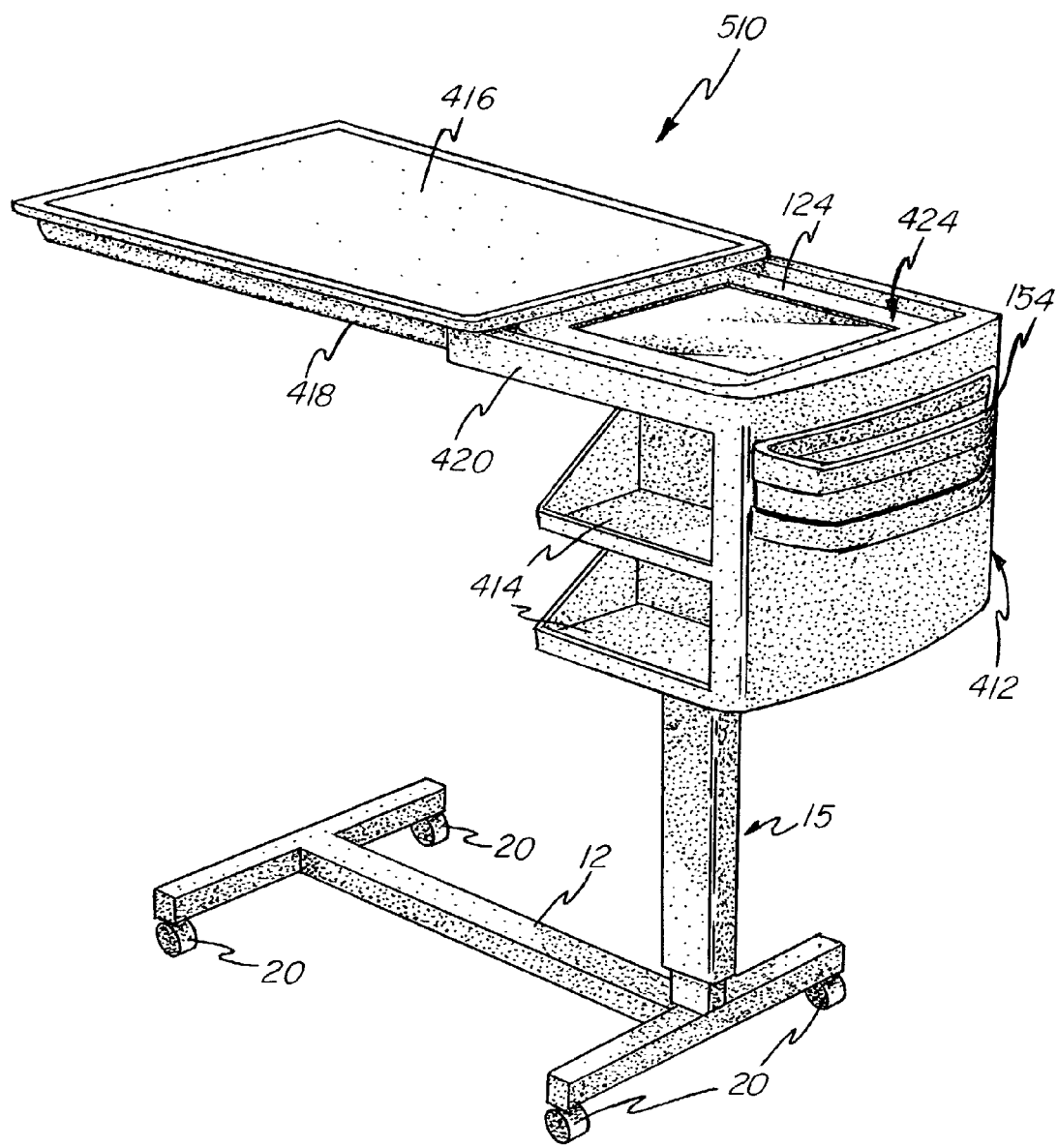
FIG. 20 is a perspective view similar to FIG. 19, illustrating the display screen in a storage position below the first table section.

Turning now to FIGS. 19 and 20, a further embodiment of overbed table 510 is illustrated as including a storage unit 412 including a storage cavity or recess 424 similar to that disclosed above with respect to the overbed table 410. The display device 124 in the overbed table 510 is pivotally connected to the storage unit 412 through a hinge 512. As such, the display device 124 may be pivoted about a horizontal axis 514 between a use position where the display device 124 is positioned vertically above the table section 416 (FIG. 19) and a storage position wherein the display device 124 is received within the storage cavity 424 and below the horizontal plane of the table section 416 (FIG. 20).

Figure 21:
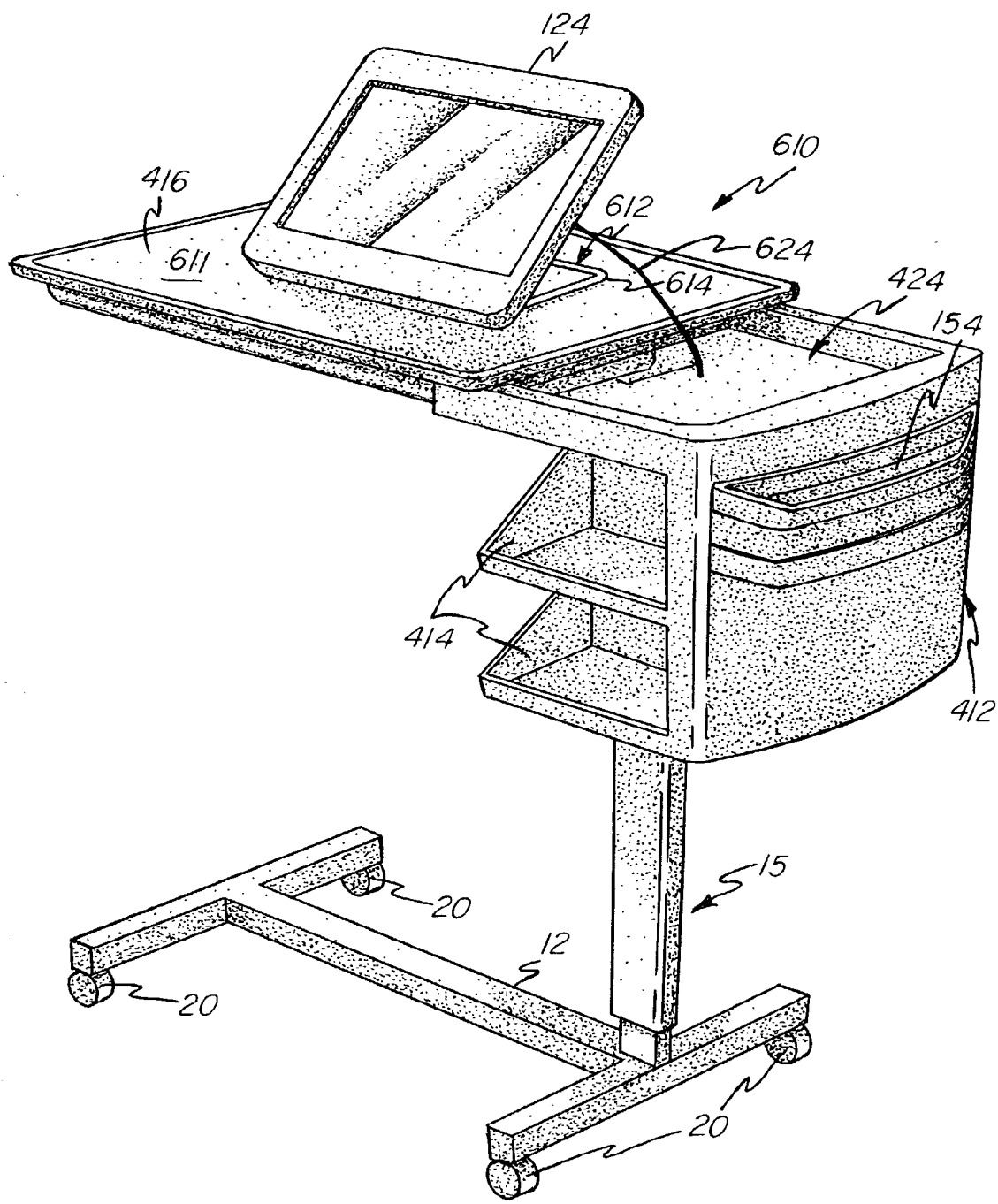
FIG. 21 is a front perspective view of a further illustrative embodiment overbed table of the present invention, illustrating a display screen configured to be removably supported within a storage compartment below the table section in a storage position and supported on the table section in a use position.
Figure 22:
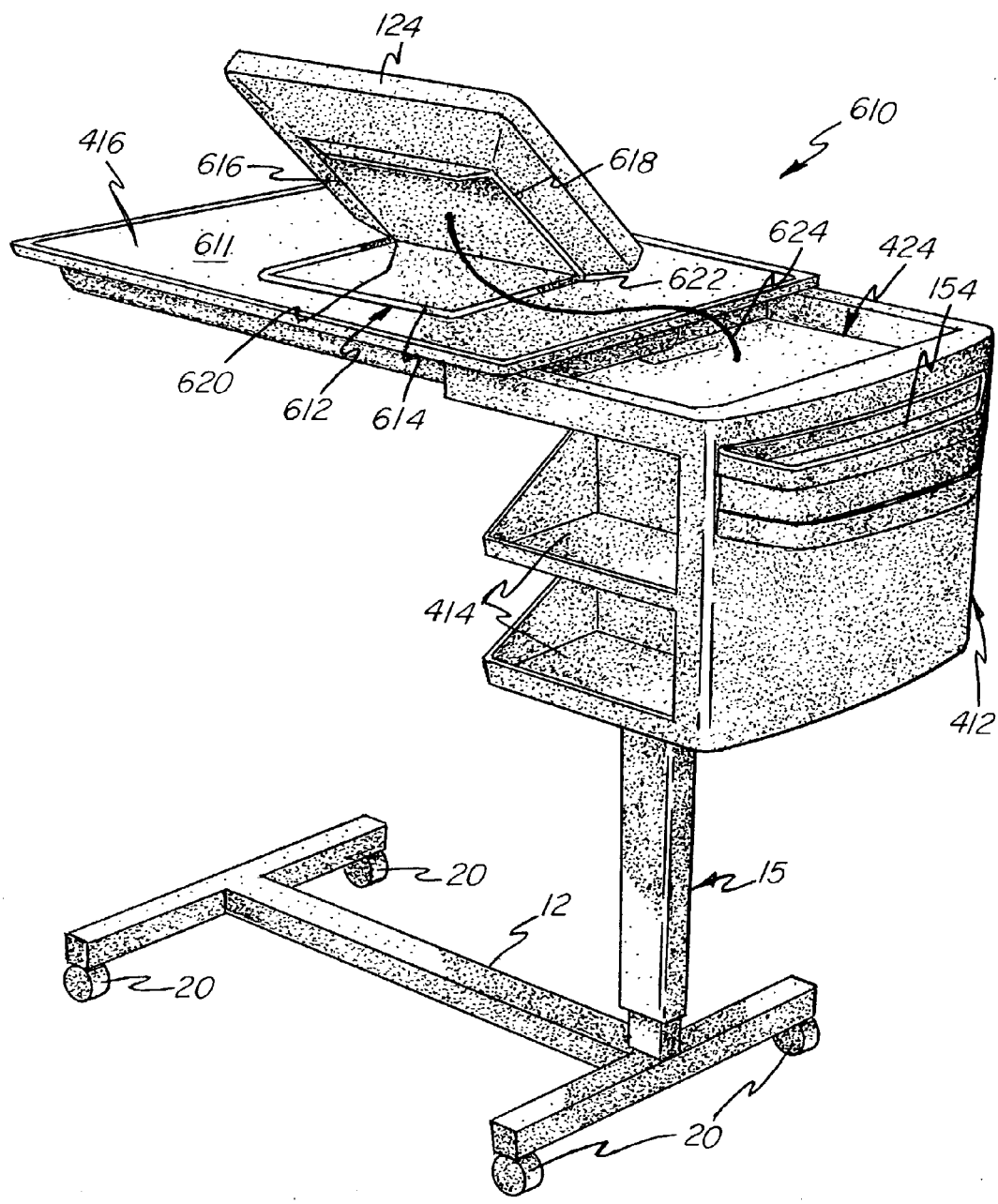
FIG. 22 is a perspective view of the display screen similar to that of FIG. 21 with the display screen rotated 180° about a vertical axis.

Turning now to FIGS. 21 and 22, a further embodiment of overbed table 610 is illustrated as again including a storage unit 412 including a storage cavity 424 similar to that detailed above with respect to the overbed table 410. The display device 124 is removably supported within the storage cavity 424. Moreover, the display device 124 may be physically removed from the storage cavity 424 and supported upon an upper surface 611 of the first table section 416 when in a use position (FIGS. 21 and 22). The display device includes a collapsible stand 612 including a base 614 and at least one upright 618 connected to a rear surface 616 of the display device 124. The base 614 and the upright 618 are operably connected through a pair of pivots or hinges 620 and 622 so that the base 614 may be folded into proximity with the uprights 616 and 618 for storage within the storage cavity 424. A conventional wire or cable 624 operably connects the display device 124 to the processor 154.

Another embodiment of the present invention is illustrated in FIGS. 23 and 24. The base 12 of the overbed table 710 includes a first docking connector 712 which mates with a second docking connector 714 coupled to the frame 22 of the bed 21 below the mattress 24. The first docking connector 712 coupled with second docking connector 714 may be utilized to supply electrical power to the display device 124 and to transmit information or signals thereto in a conventional manner. In a further embodiment, a retractable cord 718 is utilized to supply power to the display device 124. More particularly, the retractable cord 718 is receivable within a housing 720 supported by the bed frame 22. In a further embodiment, the overbed table 710 includes a plurality of upwardly-facing solar cells 722 supported on the base 12. The solar cells 722 are utilized to power components such as the display device 124 supported on the overbed table 710. The battery 156 may be charged through ambient light by the solar cells 720 using a conventional trickle charge. For nighttime use, a night light 724 may be provided in communication with the solar cells 722. Moreover, the night light 724 is supported by the bed frame 22 and directs light downwardly toward the solar cells 722. As such, at nighttime, the night light 724 provides a source of energy to the solar cells 722 to maintain the power for the electrical components on the overbed table 710.

Additional details regarding interaction between the overbed table 10, 710 and an external computer system are provided in pending U.S. patent application Ser. No. 09/849,580, filed May 4, 2001, U.S. Patent Application entitled "PATIENT POINT-OF-CARE COMPUTER SYSTEM", filed concurrently herewith, and U.S. Provisional Application Ser. No. 60/310,092, filed Aug. 3, 2001, all of which are assigned to the assignee of the present invention and are expressly incorporated by reference herein.

Although the invention has been described in detail with reference to certain illustrated embodiments, variations and modifications exist within the scope and spirit of the invention as described and as defined in the following claims.

The invention claimed is:

1. An overbed table comprising:
   a frame;
   a first table section coupled to said frame;
   a second table section coupled to said frame in vertical spaced relation to said first table section; and
   a display screen coupled to at least one of said first table section and said second table section and configured to move between a storage position and a use position, wherein said display screen is concealed by one of said first table section and said second table section in said storage position.

2. The overbed table of claim 1, wherein at least one of said first table section and said second table section is configured to move in a substantially horizontal plane with respect to the other of said second table section and said first table section.

3. The overbed table of claim 2, wherein said second table section is coupled to said first table section such that movement of said second table section results in sliding movement of said first table section.

4. The overbed table of claim 1, further comprising a support positioned in vertical spaced relation to said first table section, said support configured to move relative to said first table section within a substantially horizontal plane.

5. The overbed table of claim 4, wherein said support comprises an arm including at least one handle.

6. The overbed table of claim 5, wherein said arm includes first and second handles, and said display screen is supported intermediate said first and second handles.

7. The overbed table of claim 4, wherein said support is pivotably connected to said first table section.

8. The overbed table of claim 4, wherein said display screen is coupled to said support for pivoting movement about a substantially horizontal first axis.

9. The overbed table of claim 8, wherein said display screen is coupled to said support for pivoting movement about a second axis extending substantially perpendicular to said first axis.

10. The overbed table of claim 1, wherein said display screen is located intermediate said first and second table sections in said storage position and extends above said first table section in said use position.

11. The overbed table of claim 1, wherein said display screen comprises a flat panel monitor.

12. The overbed table of claim 1, wherein said display screen comprises a reflective mirror.

13. The overbed table of claim 1, further comprising a camera supported proximate said display screen.

14. The overbed table of claim 1, wherein said first table section is supported by said frame for movement between a generally vertical position and a generally horizontal position.

15. The overbed table of claim 14, wherein said second table section is releasably coupled to said first table section and said frame permits movement of said first table section between a generally vertical position and a generally horizontal position independently of said second table section.

16. The overbed table of claim 15, wherein said first table section is supported by said frame by an inner member provided on one of said frame and said first table section and an outer member provided on the other of said frame and said first table section, said inner member extending rotatably and slidably through said outer member to permit sliding movement and pivoting movement of said first table section with respect to said frame.

17. The overbed table of claim 14, further comprising a rest supported by one of said frame and said first table section, said rest configured to support said first table section in said generally horizontal position.

18. The overbed table of claim 1, wherein said frame includes a telescoping support column including an outer column portion and an inner column portion, the telescoping support column supporting said first and second table sections, and a base coupled to the telescoping support column.

19. The overbed table of claim 1, wherein said second table section is coupled to said first table section by a first pivotal coupling between said first and second table sections.

20. The overbed table of claim 19, wherein said first pivotal coupling includes a first bearing provided on one of said first and second table sections and a bearing race provided on said other of said first and second table sections, said first bearing engaging said bearing race to permit pivoting of said second table section about a first axis with respect to said first table section.

21. The overbed table of claim 1, further comprising a processor in communication with said display screen.

22. The overbed table of claim 1, further comprising a connector supported by said frame and configured to operably connect with a bed frame for placing the display screen in communication with a processor.

23. The overbed table of claim 1 further comprising a camera supported by said frame and configured to be directed toward the head end of a patient support surface.

24. The overbed table of claim 23, wherein said display screen includes a viewable surface configured to be directed toward the head end of the patient support surface.

25. The overbed table of claim 24, wherein said camera is supported by said display screen.

26. The overbed table of claim 24, further comprising a support configured to move relative to one of said first table section and said second table section within a substantially horizontal plane, said display screen being coupled to said support and configured to move between a storage position and a use position.

27. The overbed table of claim 23, further comprising a processor supported by said frame and in communication with said camera.

28. The overbed table of claim 23, further comprising a connector supported by said frame and configured to operably connect with a bed frame for placing the camera in communication with a remote processor.

29. The overbed table of claim 23, further comprising at least one solar cell supported by said frame and operably connected to said camera.

30. The overbed table of claim 29, wherein said at least one solar cell is alignable with a light source connected to the patient support surface.

31. The overbed table of claim 1 wherein said display screen comprises a display device supported by said frame and coupled to a power source, said display device including first and second sides, and a viewable surface supported by said first side and configured to be directed toward a head end of a patient support surface.

32. The overbed table of claim 31, further comprising a camera supported by said frame and configured to be directed toward the head end of the patient support.

33. The overbed table of claim 32, wherein said camera is in communication with said display device to define an electronic mirror.

34. The overbed table of claim 32, wherein said camera is supported by said display device.

35. The overbed table of claim 31, further comprising a support configured to move relative to one of said first table section and second table section within a substantially horizontal plane, said display screen device being coupled to said support and configured to move between a storage position and a use position.

36. The overbed table of claim 31, further comprising a processor supported by said frame and in communication with said display device.

37. The overbed table of claim 31, further comprising a connector supported by said frame and configured to operably connect with a bed frame for placing the display device in communication with a remote processor.

38. The overbed table of claim 31, further comprising at least one solar cell supported by said frame and operably connected to said display device.

39. The overbed table of claim 38, wherein said at least one solar cell is alignable with a light source connected to the patient support surface.

40. The overbed table of claim 31, further comprising a reflective mirror supported by said second side of said display device.

41. The overbed table of claim 4, wherein said support is coupled to said at least one of said first table section and second table section through said support.

42. An overbed table comprising:
a frame;
a first table section coupled to said frame;
a second table section coupled to said frame in vertical spaced relation to said first table section, at least one of said first table section and said second table section configured to move in a substantially horizontal plane with respect to the other of said second table section and said first table section, said second table section coupled to said first table section such that movement of said second table section results in sliding movement of said first table section; and
a display screen coupled to at least one of said first table section and said second table section and configured to move between a storage position and a use position.

43. An overbed table comprising:
a frame;
a first table section coupled to said frame;
a second table section coupled to said frame in vertical spaced relation to said first table section;
a support positioned in vertical spaced relation to said first table section, said support configured to move relative to said first table section within a substantially horizontal plane; and
a display screen coupled to at least one of said first table section and said second table section and configured to move between a storage position and a use position, said display screen coupled to said support for pivoting movement about a substantially horizontal first axis and about a second axis extending substantially perpendicular to said first axis.

44. An overbed table comprising:
a frame;
a first table section coupled to said frame;
a second table section coupled to said frame in vertical spaced relation to said first table section, wherein said first table section is supported by said frame for movement between a generally vertical position and a generally horizontal position, said second table section releasably coupled to said first table section and said frame permits movement of said first table section between a generally vertical position and a generally horizontal position independently of said second table section, wherein said first table section is supported by said frame by an inner member provided on one of said frame and said first table section and an outer member provided on the other of said frame and said first table section, said inner member extending rotatably and slidably through said outer member to permit sliding movement and pivoting movement of said first table section with respect to said frame; and
a display screen coupled to at least one of said first table section and said second table section and configured to move between a storage position and a use position.

45. An overbed table comprising:
a frame;
a first table section coupled to said frame;
a second table section coupled to said frame in vertical spaced relation to said first table section, said second table section coupled to said first table section by a first pivotal coupling between said first and second table sections, wherein said first pivotal coupling includes a first bearing provided on one of said first and second table sections and a bearing race provided on said other of said first and second table sections, said first bearing engaging said bearing race to permit pivoting of said second table section about a first axis with respect to said first table section; and
a display screen coupled to at least one of said first table section and said second table section and configured to move between a storage position and a use position.

46. The overbed table of claim 45, wherein said second table section is coupled to said frame by a second pivotal coupling between said second table section and said frame.

47. The overbed table of claim 46, wherein said second pivotal coupling includes a trunnion provided on one of said frame and said second table section and a recess provided on the other of said frame and said second table section for receiving said trunnion to permit pivoting of said second table section about a second axis with respect to said first table section, said second axis being spaced from said first axis.

48. The overbed table of claim 47, wherein said display screen is coupled to said first table section by a third pivotal coupling connected to said first table section.

49. An overbed table comprising:
a frame;
a first table section coupled to said frame;
a second table section coupled to said frame in vertical spaced relation to said first table section; and
a display screen coupled to at least one of said first table section and said second table section and configured to move between a storage position and a use position wherein said display screen is located between said first table section and said second table section in said storage position.

* * * * *